United States Patent
Sipin

(10) Patent No.: US 6,280,408 B1
(45) Date of Patent: Aug. 28, 2001

(54) CONTROLLED FLUID TRANSFER SYSTEM

(76) Inventor: Anatole J. Sipin, 221 E. 78th St., NYC, NY (US) 10021

( * ) Notice: Subject to any disclaimer, the term of this patent is extended or adjusted under 35 U.S.C. 154(b) by 0 days.

(21) Appl. No.: 09/286,400

(22) Filed: Apr. 5, 1999

Related U.S. Application Data

(63) Continuation of application No. 07/973,958, filed on Nov. 9, 1992, now abandoned.

(51) Int. Cl.$^7$ .................................................. A61M 31/00
(52) U.S. Cl. ........................................................ 604/65
(58) Field of Search .............................. 604/65, 66, 67, 604/132, 133, 140, 141, 142, 145, 146, 151, 153; 222/15, 55, 96

(56) References Cited

U.S. PATENT DOCUMENTS

| | | |
|---|---|---|
| 3,640,277 | 2/1972 | Adelberg . |
| 3,895,741 * | 7/1975 | Nugent .................................. 222/103 |
| 4,432,468 * | 2/1984 | Siff et al. ................................ 222/55 |

FOREIGN PATENT DOCUMENTS

| | | |
|---|---|---|
| 0343286 | 11/1989 | (EP) . |
| 2592306 | 7/1987 | (FR) . |

* cited by examiner

*Primary Examiner*—Sharon Kennedy
*Assistant Examiner*—Ann Y. Lam
(74) *Attorney, Agent, or Firm*—Hedman & Costigan

(57) ABSTRACT

The present invention is a closed loop system for transfer of a fluid through a line between a reservoir and a vessel in a manner to provide a flow-related parameter at a selected value. The system will have major use as a non-gravity-dependent infusion device. The system comprises a pressurizable reservoir containing a quantity of the fluid; means to control the flow of the fluid being transferred in a conduit between the reservoir and the vessel, including means to pressurize the reservoir; reference means with an output related to a selectable value of the flow-related parameter; means to measure the flow-related parameter; means to compare the outputs of the reference means and the measuring means; and means responsive to the output of the comparator means to adjust the fluid flow control means to provide the selected value of the flow-related parameter. Normally, the flow-related parameter will be the fluid flow rate in the conduit or the change of fluid volume in the reservoir.

17 Claims, 18 Drawing Sheets

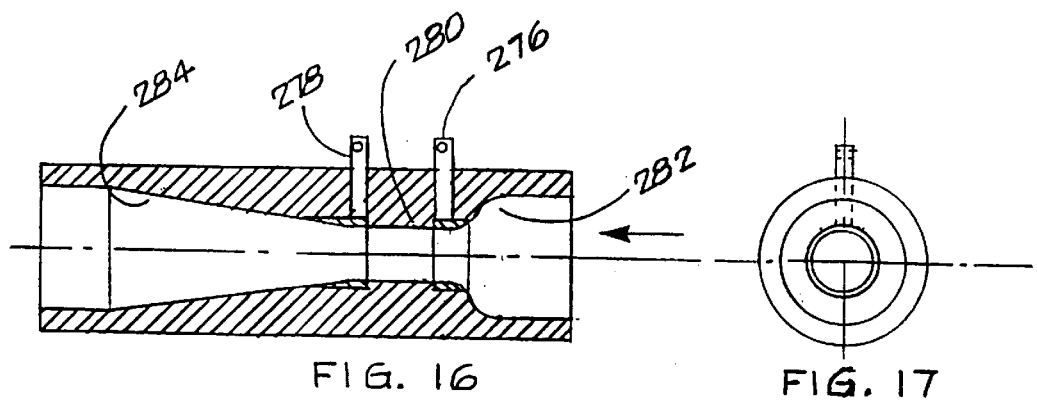
FIG. 16  FIG. 17
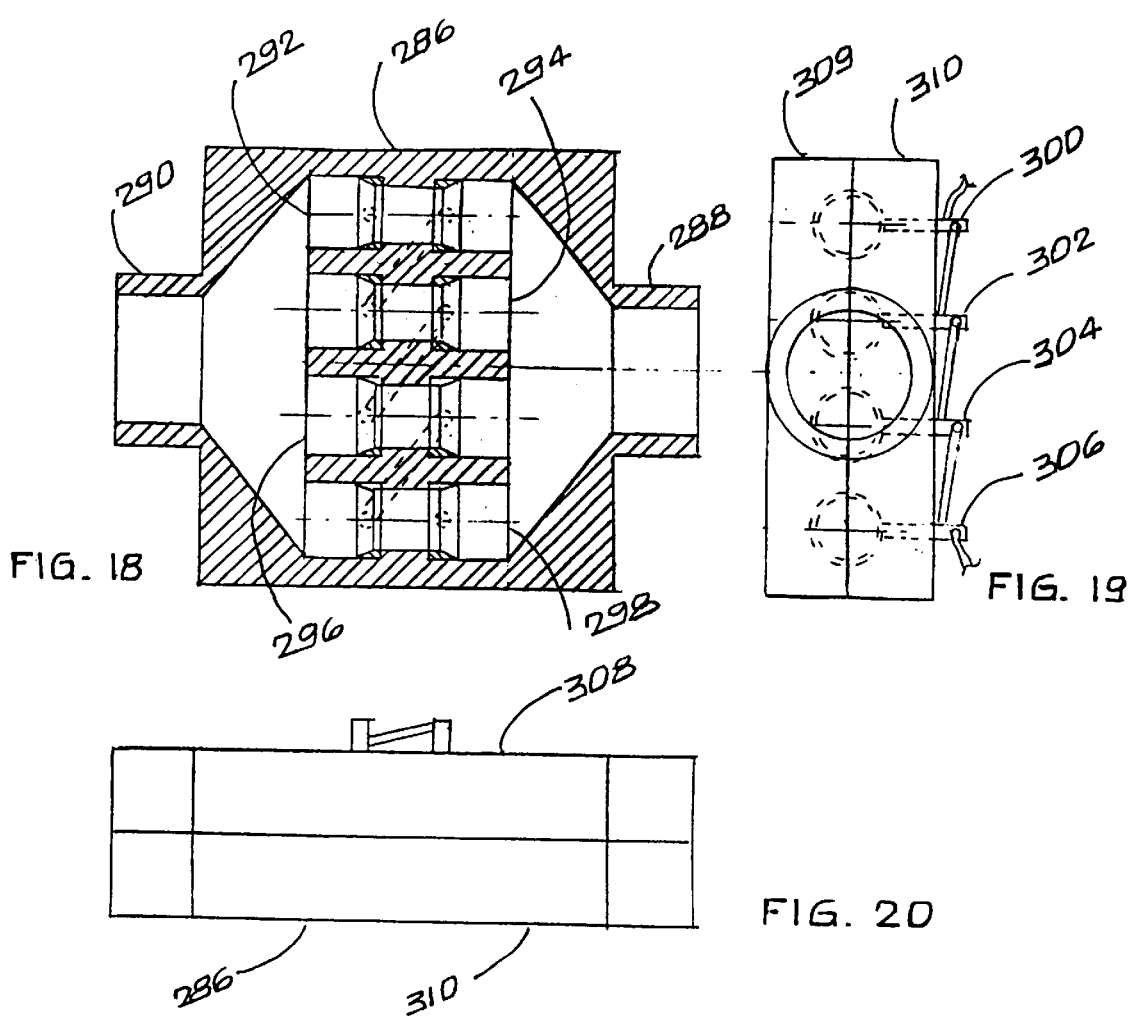
FIG. 18  FIG. 19
FIG. 20

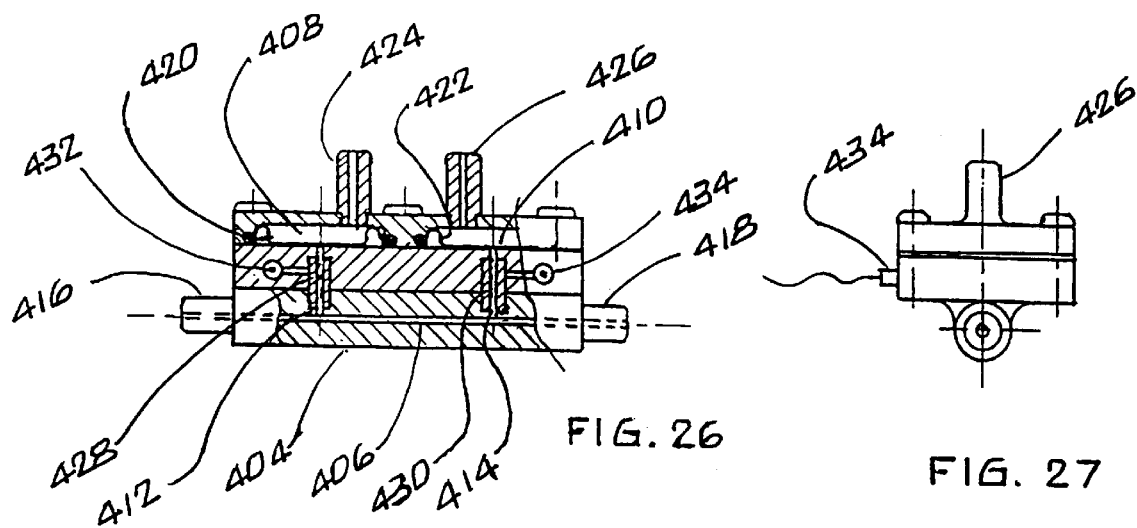
FIG. 26
FIG. 27
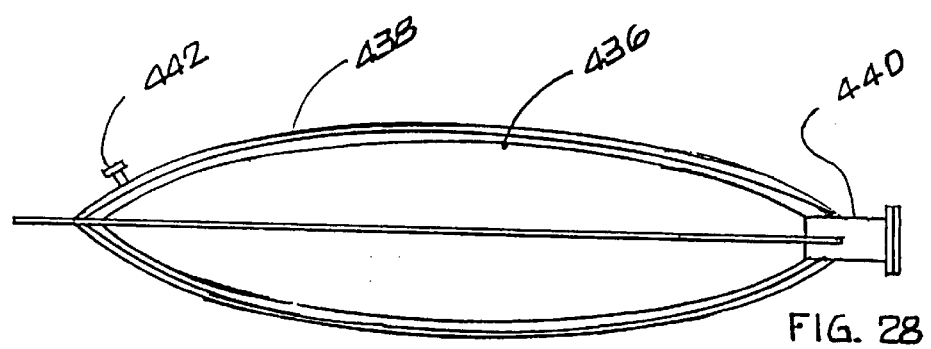
FIG. 28
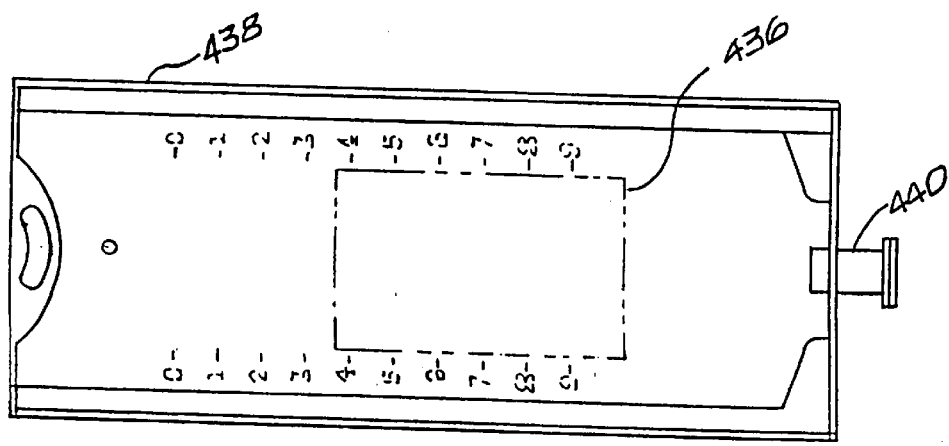
FIG. 29

CONTROLLED FLUID TRANSFER SYSTEM

This is a continuation of application Ser. No. 07/973,958, filed Nov. 9, 1992 abandoned.

BACKGROUND OF THE INVENTION

A primary application for the Controlled Fluid Transfer System will be as a Wearable Non-Gravity-Dependent Infusion Device to supply a predetermined volume of infusate at a selectable constant flow rate, without need for or disturbance due to elevation, depression or position of the IV fluid container. This will provide a substantial advantage during the movement or transport of persons for whom continuous IV infusion must be maintained, as well as for ambulatory patients. The term "wearable" signifies miniaturization to a degree that will permit the IV fluid container and the device to be carried by an ambulatory patient with a minimum of discomfort, while allowing freedom of action. The size and weight of the system will be limited by those of the container and amount of IV fluid that is carried, and the infusion device will be a minor part of the total (e.g. 25% to 40%).

Consideration of a non-gravity-dependent intravenous infusion device was originally applied to a military requirement for equipment to "deliver measured amounts of fluids at a constant reliable rate without technical supervision—for mass casualty and transport of wounded." In such situations it would be necessary to infuse drug or nutrient solutions over a period of hours in crowded areas without benefit of medical assistance. Examples of such conditions would be in evacuation aircraft or vessels, transporting a large number of individuals. What is desired is the capability to place the IV fluid container next to the individual, on the individual or on a litter, in any position or orientation, and maintain the required constant flow rate. The value of a wearable system is evident here, since it permits the individual receiving infusion to move or to be moved, with no need to detach and move the IV fluid container and infusion device separately.

It is also appreciated that there are comparable requirements for a wearable, or miniature, non-gravity-dependent infusion device for civilian applications, particularly where there is transport or movement of patients or injured individuals receiving continuous infusion. Examples are:

a) Intra-hospital transport of patients, as for periodic transport between the medical intensive care unit and a diagnostic scan facility, or from the surgical intensive care unit to the patient's room. Availability of a miniature infusion device that can be secured to the patient's bed (or the patient directly) should ease the task of the transport nurse.

b) Infusion during diagnostic procedures where rate must be controlled in different (e.g. inverted) positions (anesthesia during air contrast pneumoencephalography).

c) Transport of patients between hospitals or treatment centers.

d) Emergency transport of seriously injured individuals from remote or inaccessible locations, as by a litter secured to a helicopter. A wearable infusion device attached directly to the individual is advantageous, as it will no longer be a factor in moving the injured person.

e) Evacuation of injured from the scenes of disasters, such as fires, explosions, storms, earthquakes. The situations could be similar to the military conditions discussed above.

f) Total parenteral nutrition. For patients who require continuous parenteral infusion of nutrients in a hospital setting, and who otherwise could be ambulatory, a wearable infusion device would provide freedom from attachment to immobile equipment. For the majority of patients who undergo parenteral feeding at home, the time of infusion of the TPN solution is between 8 and 14 hours, mostly at night. Where the required duration is greater than the sleep period, a wearable infusion device will be advantageous, as it will permit normal movement and activity for the remainder of the infusion time.

In present clinical applications, where infusion with gravity lines and manual flow clamps is inadequate, an infusion pump or controller will be used. Controllers, in effect, automate the procedure normally followed with manual, gravity-fed administration sets. Usually, the drop rate of IV fluid into the drop chamber is sensed photo-optically, and an IV line clamp is automatically adjusted to maintain the drop rate constant at the selected value. The actual flow rate depends not only on the drop rate but also on the drop size, which varies with the viscosity and surface tension of the particular fluid being administered, and the type of fluid must be taken into account for an accurate determination of flow rate. The maximum flow obtained with a controller is the same as that of a simple gravity feed; and the flow rate is sensitive to back pressure and container height.

Pumps can provide the desired flow rate without requiring a gravity head for the IV supply; they also can pump against a much higher back pressure that could be required by small-pore filters or intra-arterial infusions. Pumps are usually of the peristaltic types or reciprocating displacement types with replaceable cassettes (Abbott, IMED, IVAC). Although current infusion pumps are of the displacement type, there is still an effect of gravity head on flow rate, which varies depending on the pump. Also, the weights of commercial pumps are relatively high, and the sizes and weights of these pumps are disadvantages for their use in non-gravity-dependent field or wearable applications.

In accordance with the teachings of the new Controlled Fluid Transfer System, a Non-Gravity-Dependent Infusion Device will include a pressurizable reservoir to contain the (IV) fluid and means to measure and adjust the flow of the fluid by a closed loop control, including pressurization of the reservoir, to provide a selected value of flow rate.

Trapped air in commercial infusion bags and bottles, which are only partially filled with infusion fluid, can present a problem for their use in a pressurized, non-gravity-dependent infusion system. In conventional gravity-feed infusion procedures, the fluid container is hung with the outlet at the bottom, and the air retained in the container rises to the top, where it remains during the procedure. The liquid in the fluid transfer line is under positive pressure, and there is little danger of the trapped air entering the line. In a non-gravity-dependent infusion system, however, the fluid filled container could be placed in any position or orientation and the trapped air could just as well collect at the container outlet as elsewhere. Means must be provided, therefore, to remove any air that enters the line from the container, either by an initial air removal procedure, use of an in-line air trap, or both. An air trap should be included in any event to remove small air bubbles that cling to the walls of the container and that could enter the transfer line. Also, since there is some prospect of an air bubble traveling down the fluid transfer line to the needle, an air-in-line detector should be provided, as is required for information pumps, in which air could leak into the system due to negative pressure at the pump inlet.

A number of infusion devices have been described in which the IV fluid is delivered from a flexible container at a purportedly constant flow rate through pressurization of the container.

In U.S. Pat. No. 3,640,277 to Adelberg, the driven fluid is retained in a container having a collapsible volume which is pressurized by a driving fluid. The driving fluid is administered from a pressure regulator through a selectable flow restrictor, which determines the flow rate of the driven fluid.

Olson in U.S. Pat. No. 4,337,769 shows a liquid administration device in which the liquid is contained in a flexible, collapsible bag, which is located in a housing filled with compressed cellular material. The cellular material exerts pressure on the collapsible bag to drive the liquid, whose flow rate is governed by a valve.

U.S. Pat. No. 4,857,055 to Wang shows a compression device in which a flexible solution container is positioned evenly between two inflatable sacs within a rigid casing. The sacs can be inflated by an aerosol to provide constant pressurization of the container, depending on temperature. Selectable capillary flow moderators in the delivery line determine the solution flow rate.

In a Portable Infusion Device shown in U.S. Pat. No. 5,059,182 to Laing, an air pressure bladder is in intimate contact with a flexible solution reservoir within the housing. The air pressure bladder has a volume at least five times that of the reservoir. A flow restrictor determines the flow rate of the solution. The increase in air volume in the bladder due to discharge of the solution from the reservoir is limited in relation to the original volume, limiting the decline in air pressure and the change in flow rate during delivery.

All of these prior devices use open loop systems, in which the fluid is forced through a restrictor by more or less constant pressurization of a flexible fluid reservoir. There is no simple way of adjusting flow rate to accommodate different needle resistances except by prior calibration to determine pressurization level, where this is adjustable, or restrictor size. The devices count on low venous pressures, in which changes will not greatly affect the overall pressure drop. But the devices are not suitable for arterial infusion where the pressure levels are elevated and variable.

Also, in none of the prior art devices described above, is there any recognition of the potential problem presented by air retained in the fluid container, or any illustration or discussion of air removal procedures or devices, or air-in-line detectors.

SUMMARY OF THE INVENTION

In its most general form, the invention is a closed loop system for transfer of a fluid through a line between a reservoir and a vessel in a manner to provide a flow-related parameter at a selected value. The system comprises a pressurizable reservoir containing a quantity of the fluid; means to control the flow of the fluid being transferred in a conduit between the reservoir and the vessel, including means to pressurize the reservoir; reference means with an output related to a selectable value of the flow-related parameter; means to measure the flow-related parameter; means to compare the outputs of the reference means and the measuring means; and means responsive to the output of the comparator means to adjust the fluid flow control means to provide the selected value of the flow-related parameter. Normally, the flow-related parameter will be the fluid flow rate in the conduit or the change of fluid volume in the reservoir.

In a preferred embodiment, the reservoir pressurization is varied to maintain fluid flow rate at a selected value. The fluid reservoir is a container with a flexible wall, and the reservoir is pressurized through a pressure applicable with a pneumatically-actuated movable wall in contact with a flexible wall of the container the applicator is connected to a source of variable positive pressure that applies pressure to the fluid in the container through the movable wall of the pressure applicator and the flexible wall of the container. The flow-related parameter is the fluid flow rate in the fluid conduit, and the measuring device include means, having an output, to measure the rate of flow of the fluid through the conduit. The measuring device could include a laminar flow measuring restrictor in the fluid transfer conduit and a transducer with an electrical output related to the fluid pressure drop across the restrictor as a measure of the flow rate of the fluid.

Preferably, the outputs of the reference means, the measuring device and the comparator are electrical signals, and the flow controller includes a microcomputer.

When the system is used as a non-gravity-dependent infusion device, means are supplied in the fluid transfer conduit to effectively separate gas bubbles from the infusion liquid flowing through the conduit in any orientation of the gas separating means. Also means can be provided to detect the passage of gas bubbles in the liquid flowing through the conduit.

Novel means for detecting the presence of gas in the electrically conductive liquid flowing through the conduit comprise a pair of electrodes, spaced apart to define a path for electrical current through the liquid between them; a source of electrical voltage connected between the electrodes; and means to sense the change in electrical impedance between the electrodes as a measure of gas present in the liquid between them.

BRIEF DESCRIPTION OF THE DRAWINGS

The following detailed description of the preferred embodiments can be understood better if reference is made to the drawings, in which:

FIG. 16 is a sectional view of another version of the gas-in-line sensor shown in FIG. 14.

FIG. 17 is an end view of the sensor shown in FIG. 16.

FIG. 18 is a sectional elevation view of a variation of the gas-in-line sensor shown in FIGS. 14 and 16, including multiple flow paths.

FIG. 19 is an end view of the sensor shown in FIG. 18.

FIG. 20 is a bottom view of the sensor shown in FIG. 18.

FIG. 26 is a sectional elevation view of a disposable fluid flow measuring restrictor with integral fluid isolating barriers.

FIG. 27 is an end view of the measuring restrictor shown in FIG. 26.

FIG. 28 is an elevation view of a disposable pressurizable fluid reservoir in an integral pressurizing container.

FIG. 29 is a plan view of the disposable integral fluid reservoir and container shown in FIG. 28.

DETAILED DESCRIPTION OF THE INVENTION

Figure 1:
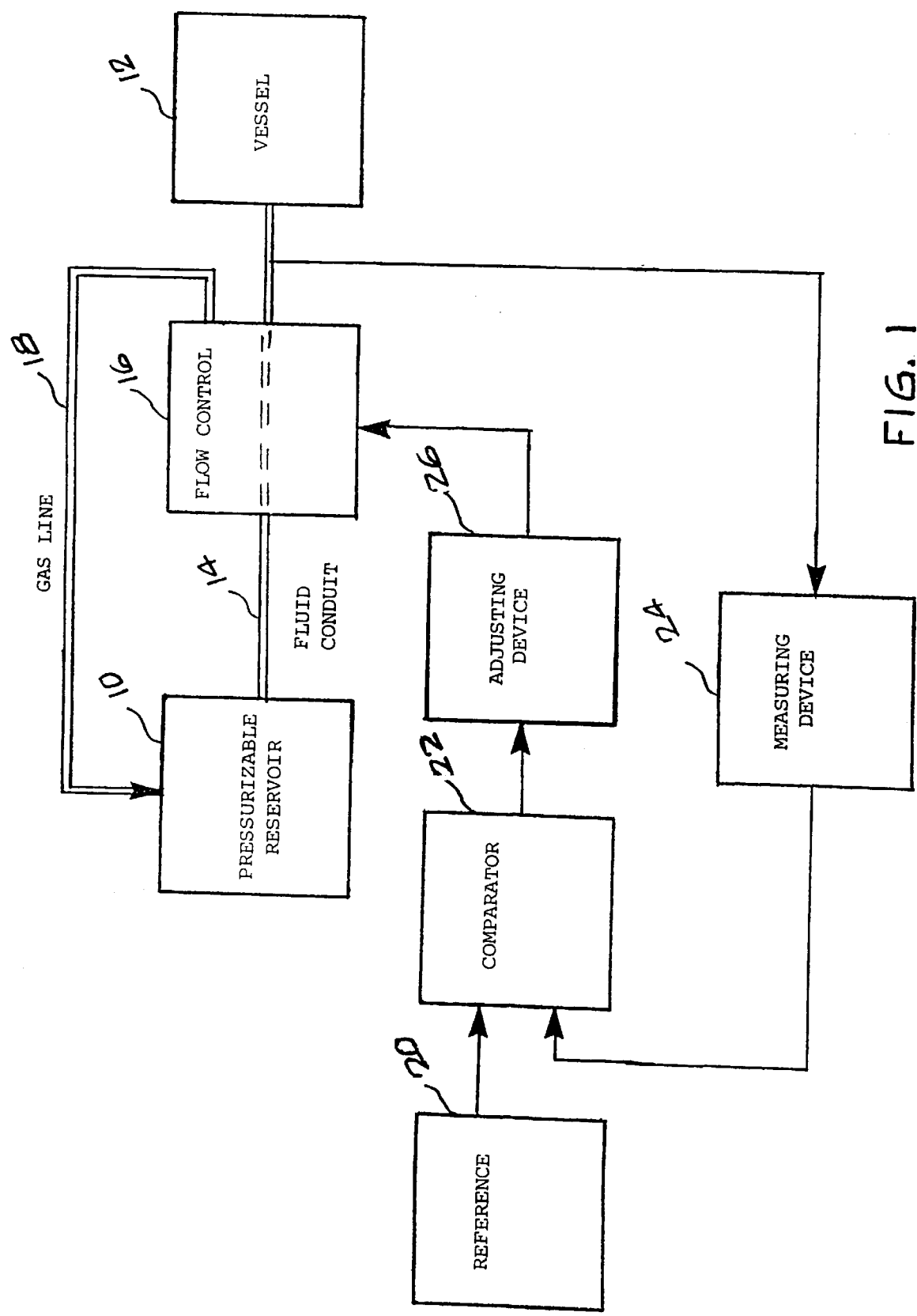
FIG. 1 is a functional block diagram of the basic fluid transfer system, illustrating the interactive relations among the major components.

FIG. 1 discloses a system for transfer of a fluid between a pressurizable reservoir 10 and a vessel 12 through a conduit 14, connected at one end to reservoir 10 and at the other end to vessel 12. A flow controller 16 applies gas pressure in a positive or negative sensor with respect to atmospheric pressure through line 18 to reservoir 10 to provide a pressure difference between the reservoir and the vessel that will cause fluid to flow through conduit 14 between the reservoir and the vessel in a direction and at a rate dependent on the sense and the magnitude of the pressure difference. Flow controller 16 may also include adjustable valve means interactive with conduit 14 to vary the resistance to flow, and thereby, the rate of fluid flow between reservoir 10 and vessel 12. A reference means 20, provides an output related to the magnitude and sense of a selectable value of the flow-rated parameter to a comparator 22. A measuring device 24 detects the flow-rated parameter and provides an output related in magnitude and sense to the flow related parameter to comparator 22. The comparator provides an output related to the difference between the outputs of reference means 20 and the measuring device 24 to an adjusting device 26 which adjusts flow controller 16, including pressurization of reservoir 10 in a direction and with a magnitude to provide the selected value of the flow-related parameter. The selected value could be of any of several parameters related to the fluid flow, such as the fluid flow rate in conduit 14, the change of fluid volume in reservoir 10, or a pressure or pressure difference. It is to be understood, also, that the diagram of FIG. 1 is functional in nature, and that the point of measurement of the flow related parameter can be at any point or points in the fluid containing members, from, and including, reservoir 10 and to, and including vessel 12.

Figure 2:
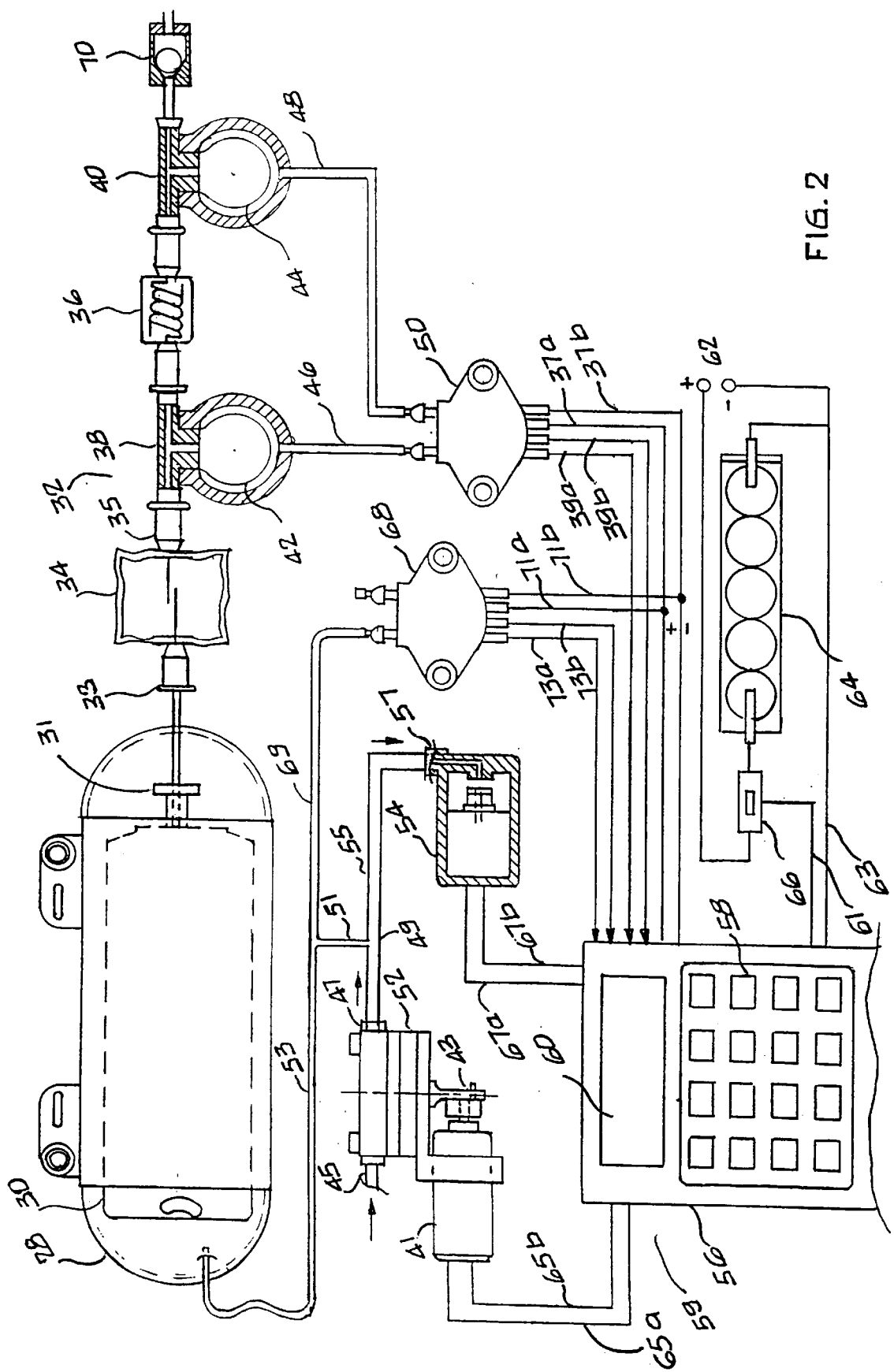
FIG. 2 is a schematic diagram of a preferred embodiment of the basic system, identified as Type C-1.

FIG. 2 discloses a preferred embodiment, whose system components and operation identified as Type C-1, which is defined as a system in which the reservoir pressurization is varied to maintain fluid flow rate at a selected value. The fluid reservoir is a container with a flexible wall, and the reservoir is pressurized through a pressure applicator with a pneumatically-actuated movable wall in contact with a flexible wall of the container. The applicator is connected to a source of variable positive pressure that applies pressure to the fluid in the container through the movable wall of the pressure applicator and the flexible wall of the container. The flow-related parameter is the fluid flow rate in fluid conduit 14, and the measuring device, 24, includes means, having an output, to measure the rate of flow of the fluid through the conduit. The measuring device used in the system shown in FIG. 2 includes a measuring restrictor in the fluid transfer conduit and a transducer with an electrical output related to the fluid pressure drop across the restrictor as a measure of the flow rate of the fluid.

A preferred type of a measuring restrictor is one that maintains laminar flow, so that the output has a linear relationship with the fluid flow rate. Other types of measuring restrictors, however, also could be used. It should be understood that the operation of the system does not depend on the measurement of the pressure drop across a restrictor. The flow rate measuring device also could utilize other methods of flow measurement.

In accordance with the teaching, the system shown in FIG. 2 is an embodiment, although not the only one, of the invention disclosed in FIG. 1, in which the output of the reference means is an electrical signal, the output of the flow-related parameter measuring device is an electrical signal, the output of the comparator is an electrical signal and the flow controller includes a microcomputer. Although the functions are uniquely described, there need not be a discrete component related to each function, as some of the functions could be performed as part of the computer program.

A typical application for the system described in FIG. 2 is for intravenous infusion of a fluid into a patient through a needle or a catheter for therapy or feeding, although there could be other applications, such as blood transfusion. Since the fluid transfer from the flexible container is due to its pressurization, a feature of the system is that it can function as a non-gravity dependent infusion device, and its performance need not be affected by orientation or elevation of the components.

Referring to FIG. 2, the system includes a pressure applicator with a movable wall, shown here as a conventional pressure cuff 28, enclosing a container with a flexible wall, shown here as a conventional infusion bag 30 filled with infusion fluid. The output 31 of the infusion fluid bag 30 is connected to an integral intravenous tubing set 32, which includes a universal air trap 34 with inlet needle 33 and outlet needle 35, and a capillary flow sensor 36 with isolating pressure taps 38 and 40. Capillary flow sensor 36 is shown as a coil of a narrow gauge hypodermic tubing, but other designs for a linear laminar flow sensor can be used.

The isolating pressure taps include flexible membranes 42 and 44 which transmit the respective infusion fluid pressures to small bore lines 46 and 48 leading to a differential pressure transducer 50. A miniature air pump 52 supplies air to pressure cuff 28 to increase the pressure of the fluid in container 30. Pump 52 is of the displacement type, which uses a diaphragm that is driven by a DC motor 41 through a piston 43 to draw atmospheric air through an inlet 45 and deliver pressurized air to cuff 28 through outlet 47 and lines 49, 51 and 53. A miniature solenoid valve 54 bleeds air from the cuff, through lines 53, 51 and 55, and valve inlet 57, to reduce the pressure of the fluid in container 30. The differential pressure across capillary flow sensor 36, and, therefore, the fluid flow rate in the intra-venous tubing set 32 are thereby maintained at a pre-selected value. Solenoid valve 54 also bleeds air from pressure cuff 28 to prevent over-pressurization of the infusion fluid bag, and it can dump the pressure to stop the flow in an emergency. The system is under the control of an electronic module 59, which includes transducer signal processing and valve and pump driving electronics, as well as a microcomputer 56, a keyboard 58 and a liquid crystal display 60. The system is powered from a DC supply through leads 61 and 63, either an external source connected to terminals 62, or a battery 64, selectable through a double-pole switch 66.

It is to be understood that air could be removed from pressure cuff 28 also by reversing the connections to the inlet 45 and the outlet 47 of air pump 52, as by a double-acting solenoid-actuated pinch valve, as well as by opening solenoid bleed valve 54. A drawback with this flow reversal is that a double-acting valve will be larger and draw more current than the bleed valve 54, and depressurization response could be slower.

In operation, the desired flow rate is entered into the computer through the keyboard. If necessary for improved accuracy, a calibration value for the capillary flow sensor and identification for the infusate fluid (or viscosity value) are also entered into the computer. Flow is controlled by the output from differential pressure transducer 50, which includes a resistive bridge that is excited by a voltage from electronic module 59 through leads 37*a* and 37*b*, and which provides an output related to the differential pressure to electronic module 59, through leads 39*a* and 39*b*. This signal is fed back and compared with the selected flow value in the computer, which then causes DC motor 41 of air pump 52 to be energized through leads 65*a* and 65*b*, or solenoid valve 54 to be energized through leads 67*a* and 67*b*, as required, to maintain the output of the differential pressure transducer 50 at the control point. Since flow is always leaving the infusion fluid bag, make-up air will normally be provided by the air pump. The major function of the air bleed solenoid valve should be as a safety relief valve.

Air pressure in cuff 28 is sensed by a gauge pressure transducer 68, through lines 53 and 69. Pressure transducer 68 also includes a resistive bridge that is excited from electronic module 59 through leads 71*a* and 71*b*, and which provides an output related to the gauge pressure to electronic module 59 through leads 73*a* and 73*b*, which output is fed also to the microcomputer. The transmembrane pressure difference between the air in the cuff and the infusion liquid in the bag is very small, as is the pressure drop across air trap 34, so that by subtracting the output of differential pressure transducer 50 from the output of gauge pressure transducer 68, an accurate determination is obtained of the infusion liquid pressure in the line before the intra-venous needle or catheter.

A value of the selected total volume of liquid to be infused can be entered through the microcomputer keyboard. This is compared with the total volume of infused liquid, which is computed as the time integral of the computed flow rate. When the computed value of the infused liquid volume exceeds the selected value, the system is shut down, and an audio/visual indication of "End of Infusion" is activated. Similarly, a value for the selected infusion period can be entered through the microcomputer keyboard. When the actual operating time exceeds this value, the system is shut down and an audio/visual indication of "End of Infusion" also is activated.

Upper and lower limit values for applicator air pressure can be selected and entered through the microcomputer keyboard. Excessive air pressure could be caused by a blockage such as crimping of the infusion line. Also, free flow, caused possibly by a break in a line connection or dislodging of the intra-venous needle, can be detected by a large drop in the air pressure. When the actual measured air pressure exceeds the selected upper value or falls below the selected lower value, the system is shut down and an audio/visual indication of "Malfunction" is activated.

No automatic clamp is necessary on the infusion line, and, since the system is non-gravity-dependent and can be placed in any orientation or elevation with respect to the patient, a negative head between the infusion bag 30 and the blood vessel could occur, causing back-flow and possible entry of blood into the infusion line. Reverse flow is prevented, however, by check valve 70, in the infusion line. Check valve 70 could be spring-loaded to prevent residual flow below a minimum pressure level if a malfunction requires rapid shut-down and reduction of pressure by opening solenoid valve 54.

Table I lists typical computer control functions for operation of the system of FIG. 2 adapted for application as a non-gravity-dependent infusion device, usually for intra-venous infusion, but also capable of intra-arterial infusion. In accordance with Table I A., selected values of infusion liquid flow rate, upper liquid flow rate threshold, total infused liquid volume, applicator upper air pressure limit, applicator lower air pressure limit and infusion period are entered into the computer memory by the keyboard. Ranges of measured values are given in Item B, equations for computed values are given in Item C, and computer instructions are listed in Item D.

TABLE

NON-GRAVITY-DEPENDENT INFUSION DEVICE - SYSTEM C-1
TYPICAL CONTROL FUNCTIONS

A Select

| | | |
|---|---|---|
| 1. Infusion liquid flow rate | $Q_L$ | 1 to 1,000 ml/hr. |
| 2. Upper liquid flow rate threshold | $\Delta Q_{LU}$ | +2% to +5% |
| 3. Total infused liquid volume | $V_{LT}$ | 150 to 1,000 ml |

TABLE-continued

NON-GRAVITY-DEPENDENT INFUSION DEVICE - SYSTEM C-1
TYPICAL CONTROL FUNCTIONS

| | | |
|---|---|---|
| 4. Applicator upper air pressure limit | $P_{LV}$ | 100 to 500 mm Hg gauge |
| 5. Applicator lower air pressure limit | $P_{LL}$ | 5 to 100 mm Hg gauge |
| 6. Infusion period | $t_I$ | 1 to 48 hours |

B Measure

| | | |
|---|---|---|
| 1. Differential pressure across measuring restrictor | $\Delta P_r$ | 5 to 50 mm Hg gauge |
| 2. Applicator air pressure | $P_{ag}$ | 50 to 500 mm Hg gauge |
| 3. Operating time | $t_o$ | 1 to 48 hours |

C Compute

| | |
|---|---|
| 1. Infusion liquid flow rate | $Q_L = {}^*C_r \Delta P_r$ |
| 2. Infused liquid volume | $V_L = \int_o^t Q_L\, dt$ |

$C_r$ = 0.2, 2.0, 20.0 (ml/hr)/mm Hg depending on restrictor.

D During Infusion Period

1. Read differential pressure across measuring restrictor, $\Delta P_r$.
2. Read applicator air pressure, $P_{ag}$.
3. Read operating time, $t_o$.
4. Compute infusion liquid flow rate, $Q_L$.
5. Compare computed liquid flow rate with selected rate.
6. If computed liquid flow rate is less than selected rate, increase air pump speed.
7. If computed liquid flow rate is greater than selected rate, decrease air pump speed.
8. Compare computed liquid flow rate with upper liquid flow rate threshold. If coputed liquid flow rate is greater than thershold value, oper solenoid air bleed valve. Shut off solenoid valve when computed liquid flow rate is less than selected rate.
9. Compute infused liquid volume, $V_L$.
10. Compared computed infused liquid volume, $V_L$, with selected value of total infused liquid volume.
11. If infused liquid volume exceeds selected value of total liquid volume, shut down air pump, actuate solenoid bleed valve and actuate "End of Infusion" audio/visual indicator.
12. Compare actual operating time with selected value of infusion period.
13. If operating time exceeds selected value of infusion period, shut down air pump, actuate solenoid valve and actuate "End of Infusion" audio/visual indicator.
14. Compare measured applicator air pressure with selected limit values. If applicator air pressure is higher than upper limit or lower than lower limit, shut down air pump, actuate solenoid bleed valve and actuate "Malfunction" audio/visual indicator.

Figure 3:
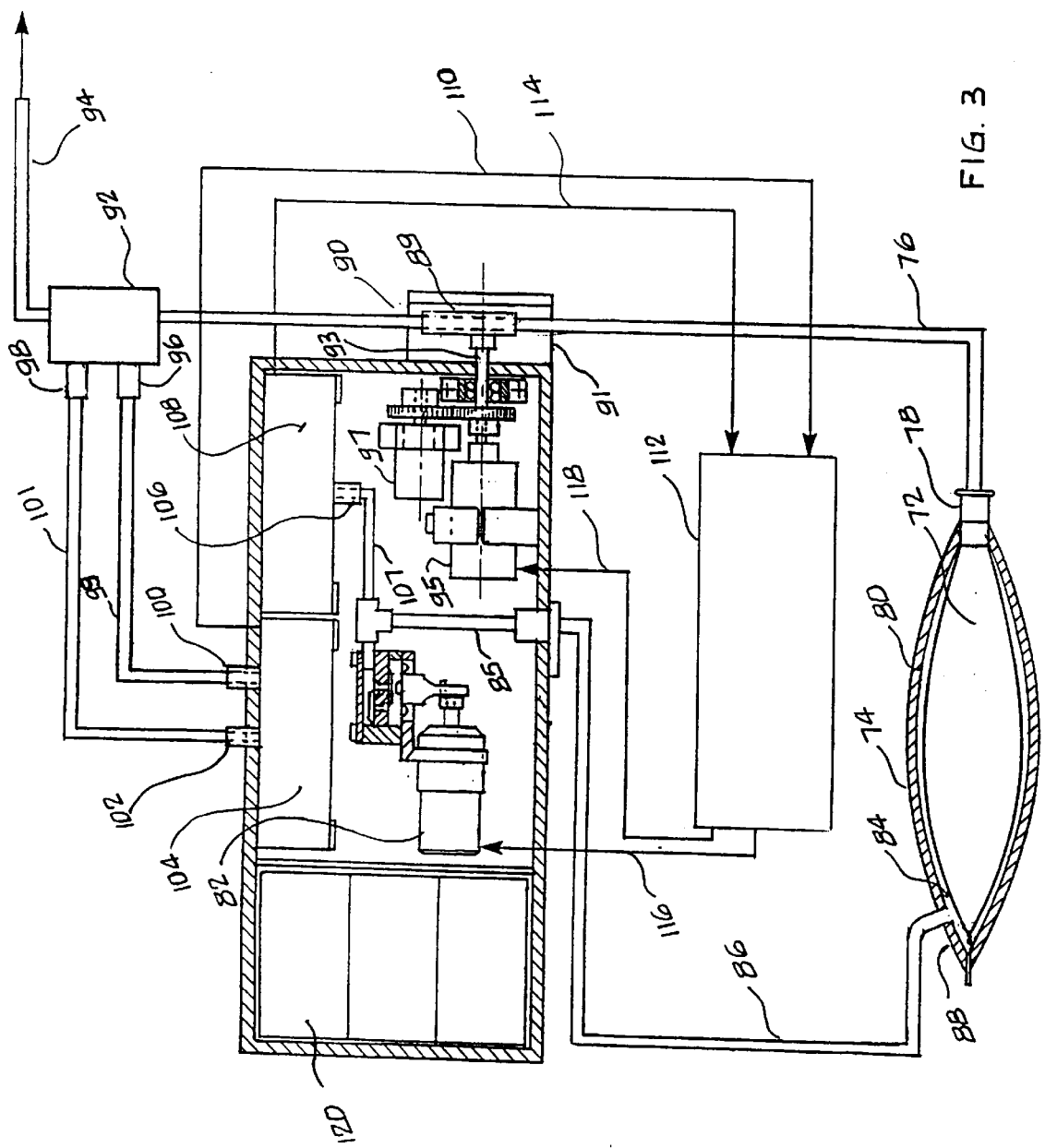
FIG. 3 is a diagram of a related embodiment identified as Type C.

Another embodiment of the invention, generally described in FIG. 1, is shown in FIG. 3, in which the pressurizable reservoir 10 includes a fluid filled container 72 with at least one flexible wall, such as a conventional intravenous fluid bag, located within a sealed, relatively rigid housing 74, and connected to a flexible tubular segment 76 of the fluid transfer conduit 14 through a seal 78 in the wall 80 of housing 74. A miniature air pump 82 performs as a source of variable pneumatic pressure by transferring pressurizing air between the pump and the interior 84 of housing 74 through 85 and line 86, which is connected to pressurizing port 88 in the wall 80 of housing 74, so as to pressurize container 72 and force the fluid to flow through flexible segment 76 of conduit 14, part of which is retained in adjustable motor-driven pinch valve 90, then through a flow measuring restrictor 92 and through conduit segment 94. Pinch valve 90 includes an eccentrically mounted cam 89, which compresses conduit segment 76 against anvil 91 by rotation of shaft 93, which is coupled to and driven by a DC gear motor 95. Shaft rotation can be sensed by a geared potentiometer 97, but this is optional. The pressure drop across restrictor 92 is fed from pressure taps 96 and 98 through lines 99 and 101 to ports 100 and 102 in differential pressure transducer 104, and the pressure in the interior 84 of housing 74 is fed to port 106 in gauge pressure transducer 108 through lines 86, 85 and 107, since the pressure drop in these lines, due to flow, is very small. The electrical output of the differential pressure transducer 104, which is related to fluid flow rate, is fed through line 110 to electronic controller 112, and the electrical output of gauge pressure transducer 108, which is related to the housing air pressure, is fed to electronic controller 112 through line 114. The output of gauge pressure transducer 108 is compared to a selected pressure reference value, and a signal related to the difference is applied to pump 82 through line 116 to adjust the pumping rate in a closed loop system so as to maintain the housing air pressure at the selected value. The output of pressure transducer 104 is compared to a selected differential pressure reference value, and a signal related to the difference is applied to gear motor 95 of pinch valve 90 through line 118 to adjust the position of the pinch valve cam 89 to maintain a constant fluid flow rate at the selected value. As shown, the system is energized from a self-contained battery 120. Use of a valve to directly control the flow of fluid in the conduit achieves a faster response than only the adjustment of reservoir pressure, and it permits immediate cessation of flow in the event of an emergency.

The system illustrated in FIG. 3, in which the reservoir pressurization is maintained at a constant value, and a valve in the fluid conduit is adjusted to maintain fluid flow rate at a constant value, is identified as Type C.

Figure 4:
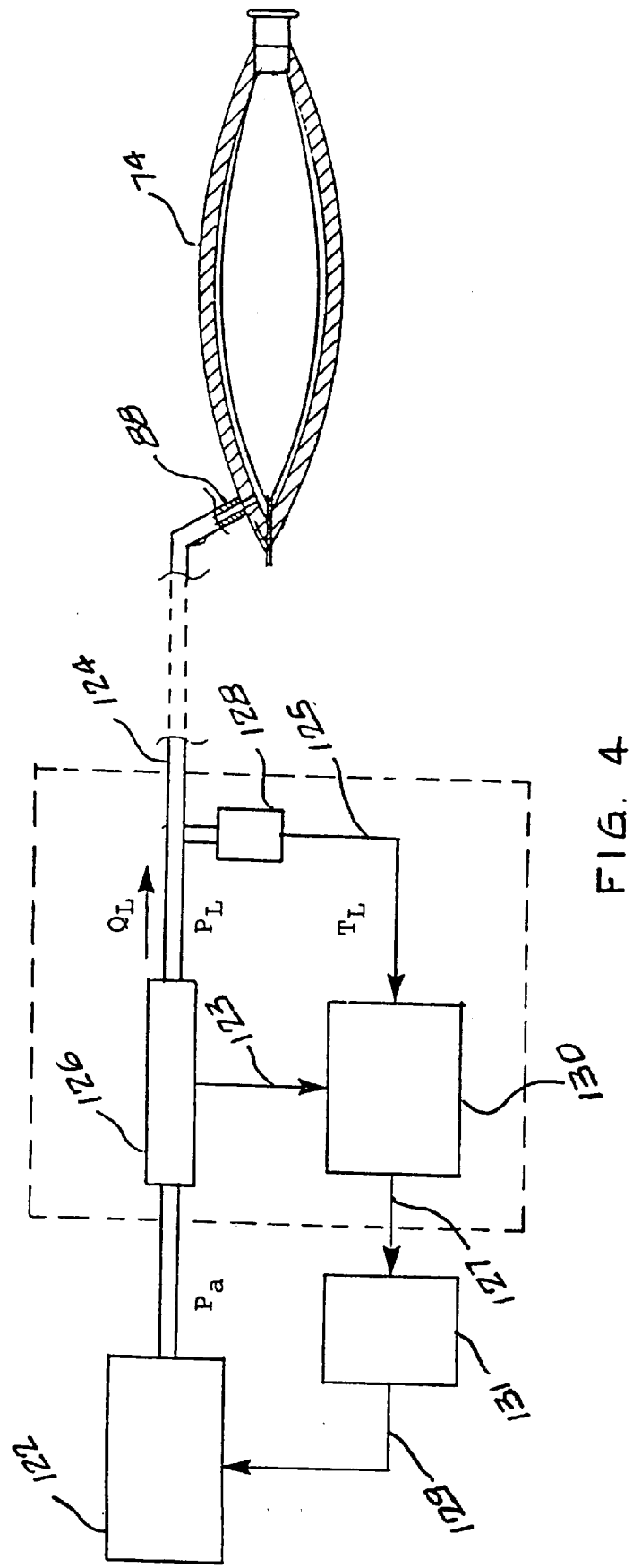
FIG. 4 is a block diagram of another system embodiment identified as Type A-1.
Figure 5:
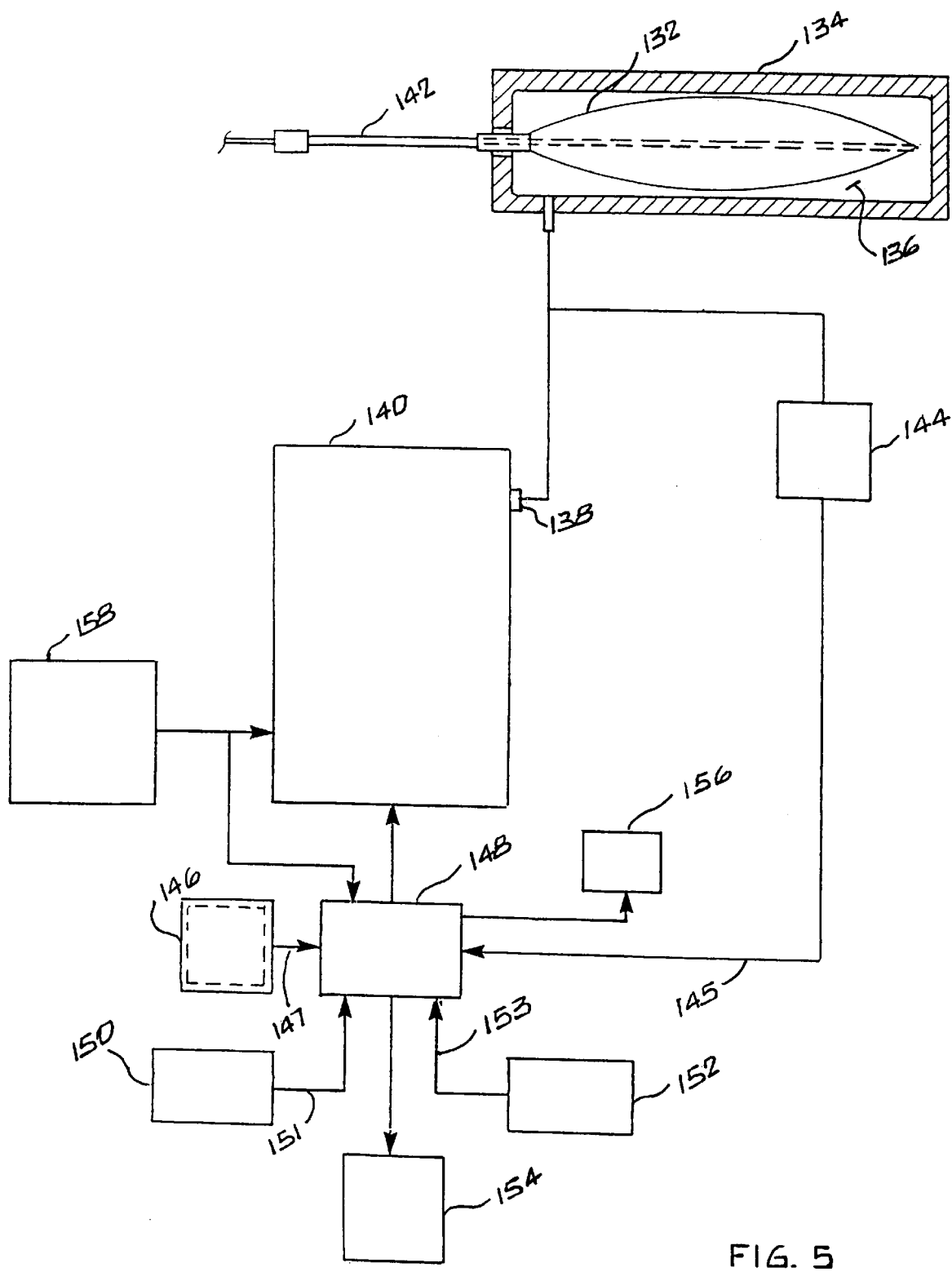
FIG. 5 is a block diagram showing a variation of the system in FIG. 4.

FIGS. 4 and 5 show a variation of the embodiment of FIG. 3, in which there is no flow measuring or flow controlling element in the fluid conduit, and the fluid flow rate and control of fluid transfer between the pressurizable container and the vessel are determined solely by measurement and control of parameters associated with the housing pressurizing gas. This system is identified as Type A-1.

The method takes into account all pneumatic parameters whose relationships can be used to accurately compute the volume of fluid displaced by a container with a movable wall within a sealed, relatively rigid housing that is pressurized by a gas from a variable source. It requires continuous measurement of the volumetric flow rate and pressure of the gas in the transfer line between the source and the container housing. The analog outputs of the measuring devices are digitized and fed to a computer, where the volume of fluid displaced by the container is determined by adding (or subtracting) the mass of air supplied to the container housing, which is required to change the pressure of the mass of air within the housing, from the total supplied air, in order to obtain the mass, hence, volume, which is used to displace the fluid in the container.

The Type A-1 system shown in FIG. 4 includes means to measure the volumetric flow rate of the fluid in the fluid transfer conduit, which comprise means, having an output, to measure the volumetric flow rate of the gas in the gas transfer line, at a location in the line where the difference between the gas pressure at the flow rate measuring location and the gas pressure in the interior of the housing is small in comparison with their absolute values, and the difference between the gas temperature at the flow rate measuring location and the gas temperature in the interior of the housing is small compared to their absolute values; means, having an output, to measure the gas pressure in the gas transfer line between the flow rate measuring location and the port in the wall of the housing; and means, having an output, responsive to the outputs of the gas flow rate measuring means and the gas pressure measuring means to compute the volumetric flow rate of the fluid in the fluid transfer conduit in accordance with the following equations:

$$Q_f = Q_L - (V_h/P_g)(dP_g/dt) \quad (1)$$

$$V_h = V_o + \int_o^t Q_f \, dt \quad (2)$$

Where $Q_f$ is the computed volumetric flow rate of the fluid in the fluid transfer line, $Q_L$ is the measured volumetric flow rate of the gas in the gas transfer line at the flow rate measuring location, $V_h$ is the volume occupied by the gas in the housing, exterior to the reservoir, $P_g$ is the measured gas pressure, and $V_o$ is the residual volume occupied by the gas in the housing when the reservoir is full. Means, having an output, can be provided to compute the volume of the fluid transferred through the fluid transfer conduit means as the time integral of the computed fluid volumetric flow rate.

Combining equations (1) and (2) yields equation (3) for the volume of fluid transferred, $V_f$:

$$V_f = \int_o^t Q_L \, dt - \int_o^t \left[ \left( V_o + \int_o^t Q_f \, dt \right) \Big/ P_g \right] (dP_g/dt) \, dt \quad (3)$$

It can be seen that solution of equation (3) is an iterative process in which the volume that is calculated in one interval is used to modify the equation in the next interval. It is necessary to known the initial residual volume of the housing, which can be a given value if all housings and line of the same types have closely corresponding characteristics. Alternatively, the value can be determined by a simple pneumatic procedure.

Referring to the right side of equation (3), it is seen that the first term is the total volume of gas passing through the gas transfer line, and the second term represents that portion of the line gas volume that increases (in the case of pressurization) the mass of gas within the housing to raise its pressure. If the two terms are equal, the transferred volume of fluid is seen to be zero, that is, the volumetric gas flow rate in the line, that is measured, is due only to pressurization of the residual volume in the housing. The pressurization volume that is added through the transfer line is equal to the time integral of the total volume in the housing multiplied by the rate of change of gas pressure in the housing. At any instant the total volume equals the residual volume (i.e. gas volume in the housing, and transfer line when the fluid side of the container is totally filled) plus the additional gas volume due to decrease of fluid volume in the housing caused by fluid ejection. This term in the equation is expressed as $V_o + Q_f dt$. If the gas pressure in the housing can be maintained at a constant value during ejection of fluid, the rate of change of pressure ($dP_g/dt$) is zero, the second term of equation (3) becomes zero, an the transferred volume of fluid equals the time integral of the measured volumetric flow rate in the line (more precisely, the volumetric flow rate in the housing).

Referring to the diagram shown in FIG. 4, the system includes a variable source of gas pressure 122 connected to port 88 of container housing 74 through a gas transfer line 124, a volumetric flow sensor 126 in gas transfer line 124, a gas pressure transducer 128 a microcomputer 130, and a flow controller 131. Volumetric gas flow sensor 126 can be of any type, including a dynamic square law orifice type of meter, as long as the signal is processed so that the final output is linearly related to the volumetric air flow rate in line 124 to the housing. It is not necessary that the meter be insensitive to pressure, as the pressure is measured as part of the system, and the pressure is available for any signal processing in the microcomputer that is required. If the difference between temperatures at the measuring location and the interior of the housing is substantial, temperature sensors can be included, and their outputs fed to the microcomputer. Microcomputer 130 accepts a signal related to volumetric gas flow rate from gas flow sensor 126 through lead 123 and a signal related to gas pressure from transducer 128 through lead 125. The microcomputer feeds a signal related to the difference between the selected and computed values of the fluid flow related parameter (flow rate or volume) to controller 131 through lead 127, and the controller feeds a signal related to the error to gas pressure source 122 through lead 129 to vary the gas pressure so as to restore the fluid flow related parameter to its selected value.

The system shown in FIG. 5 is another embodiment where the reservoir pressurizing means are adjusted to provide the selected value of the fluid flow rate, as in an intravenous (IV) infusion device that uses a miniature air pump to pressurize an IV fluid container. The IV fluid is contained in a distensible container 132 made of a suitable flexible film or elastomer. The container is assembled into an impervious rigid housing (or inelastic bag) 134, and sealed from the atmosphere. The interior of the housing surrounding the container is connected to the outlet port 138 of the miniature air pump 140. Controlled air flow from the pump pressurizes the interior of the housing and drives the fluid from the container into the IV tubing 142.

The air pump (which is shown as a block in FIG. 4) is of a positive displacement type, either a sliding piston type, similar to commercially available syringe pumps, or a diaphragm type.

All of the controls are on the air side. Container air pressure and ambient pressure are sensed by miniature transducers 144 and 146 which feed pressure-related signals through leads 145 and 147 to an electronic control 148. The electronic control 148 includes a microprocessor which combines the desired flow rate signal, pump calibration data and the pressure data to calculate the change in the actual air volume within the container (at container pressure), and which changes the pump speed to maintain the rate of change of air volume at the selected value. The rate of change of the IV fluid volume within the container is numerically equal to the rate of change of the air volume within the container, and, therefore, the IV fluid flow rate is also maintained at a constant selected value. Flow rate is set by adjustment of flow rate selector 150, which feeds a flow rate reference signal to electronic control 148 through lead 151. Delivered volume is set by adjustment of volume selector 152, which feeds a volume reference signal to electronic control 148 through lead 153. Values of important parameters are indicated on a display 154.

Neglecting second order effects, the rate of change of container air volume, which equals the air flow rate, can be expressed as: $Q_c = K_Q N P_a / P_c$ where $Q_c$=air flow rate, $P_a$=absolute ambient pressure, $P_c$=absolute chamber pressure, N=pump speed and $K_Q$ is a constant. This is proportional to the mass flow rate divided by the container pressure. By controlling the ratio of pump speed to container pressure at a constant value, the air flow and the IV fluid flow rate are also maintained at a constant value.

If there is a change in elevation of the fluid container or a change in resistance of the IV line, changing the IV fluid flow rate, the air pressure in the container will change. This will be detected by the container pressure sensor, which will adjust the pump speed to restore the actual air volume flow rate in the container and, therefore, the IV fluid volume flow rate to the desired value.

If there is an excessive occlusion or excessive flow, the control will cause the air pressure to exceed a higher or lower limit, which will shut off the pump and actuate an alarm 156. Also, the control will calculate total delivered volume and similarly shut off the pump and actuate the alarm when this exceeds a selected value.

The ambient pressure sensor makes the flow rate computation insensitive to changes in altitude. The infusion device, therefore, can be used at high altitudes and pressurized aircraft cabins without loss of accuracy.

The portable system is energized by a battery 158.

Figure 6:
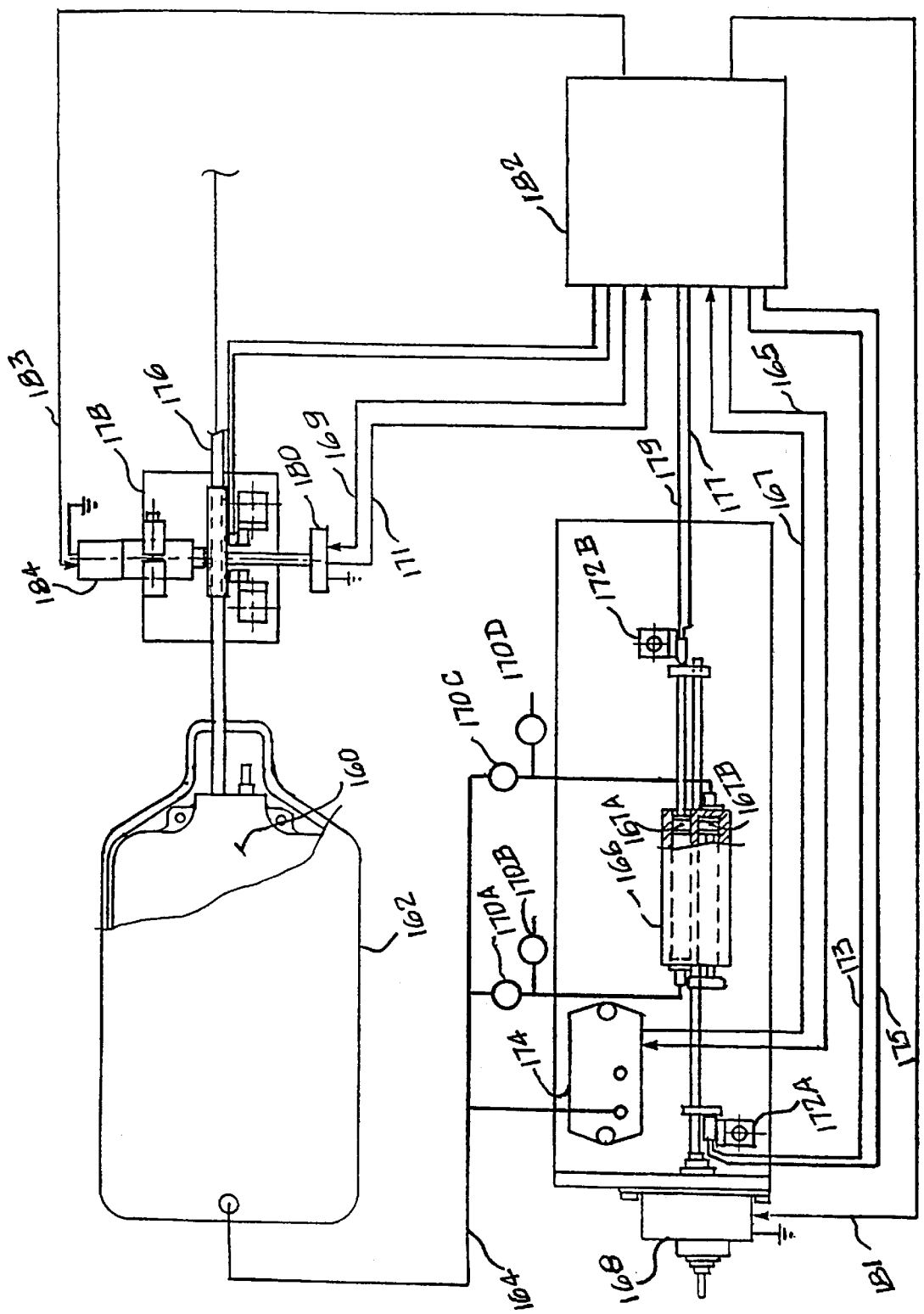
FIG. 6 is a schematic diagram of an embodiment related to those shown in FIG. 4 and FIG. 5, and identified as Type A.

FIG. 6 discloses an embodiment which is an example of a system identified as Type A. In this mode of operation, a displacement type of air pump adds air to the interior of the rigid housing containing a flexible container, at a selected constant mass rate of flow. A motorized pinch valve varies the occlusion of the fluid transfer line, which passes fluid from the container, in a closed loop control, which, by varying the resistance to fluid flow, maintains the housing air pressure at a constant value. A constant mass flow of air into the housing at a constant air pressure is equivalent to a constant increase of air volume within the housing, and equilibrium only can be maintained if there is an equivalent constant decrease of fluid volume. This is accomplished by the variable pinch valve. The control of System A, therefore, requires no measurement or pumping devices on the fluid side, and flow control can be maintained with a simple length of continuous tubing between the pressurizable reservoir and the vessel.

In the embodiment shown in FIG. 6, a flexible fluid container 160 is located within a rigid housing 162, the interior of which is pressurized through an air line 164 by a bi-directional syringe pump 166, consisting of dual syringes 167A and 167B, which are driven by a linear actuator 168. Unidirectional air flow in line 164 is maintained by electrically-operated directional valves 170 A, B, C and D which are actuated at the end of each stroke through limit switches 172 A and B. During pressurization of housing 162, when syringes 167A and B are being driven to the left, valve 170A is open and valve 170B is closed and syringe 167A is forcing air into line 64. Simultaneously, valve 170C is closed and 170D is open and syringe 167B is drawing air from atmosphere through valve 170D. In the opposite direction of syringe travel, the state of the valves is reversed and air is pumped into line 64 by syringe 167B so that line 164 is continuously pressurized. By reversing the state of the valves in relation to the direction of valve travel, air is continuously drawn from line 164, and housing 162 is continuously depressurized. The housing air pressure is sensed by a transducer 174. Fluid flow through transfer line 176 is varied through its occlusion by motor-driven pinch valve 178 to maintain the housing air pressure at a constant value. Pinch valve 178 is similar in construction to pinch valve 90, shown in FIG. 3. The degree of occlusion is measured by valve position sensor 180. The outputs of transducer 174, valve position sensor 180 and switches 172 are fed through leads 165 and 167, leads 169 and 171 and leads 173, 175, 177 and 179 to a microcomputerized control 182 which drives the linear actuator 168 through lead 181 and adjusts the pinch valve motor 184 through lead 183 to maintain the fluid flow rate at the selected value.

The embodiment of FIG. 6 can also be operated in a mode identified as Type B, which is similar to Type A operation in that it does not require any measuring elements in the fluid side, control of fluid flow being determined by air flow rate, the housing air pressure, and the position of the pinch valve. In System B, the housing pressure cycles in a narrow band between an upper and a lower limit. Air can be supplied intermittently at a high rate until the pressure reaches the upper limit, at which time the air flow is shut off. The chamber pressure decreases due to the fluid flow from the container until it reaches the lower limit, at which time air flow is turned on again. If the air volume is known, the increment of volume, which is directly related to the air volume and inversely related to the constant pressure differential is also known. The time for the pressure to decay from the upper limit to the lower limit, then, is a direct measure of the fluid volume flow rate. The chamber air volume can be determined by measuring the total displacement (e.g. number of strokes) required to pump the chamber to the known operating pressure (initial volume) and summing the increments.

Figure 7:
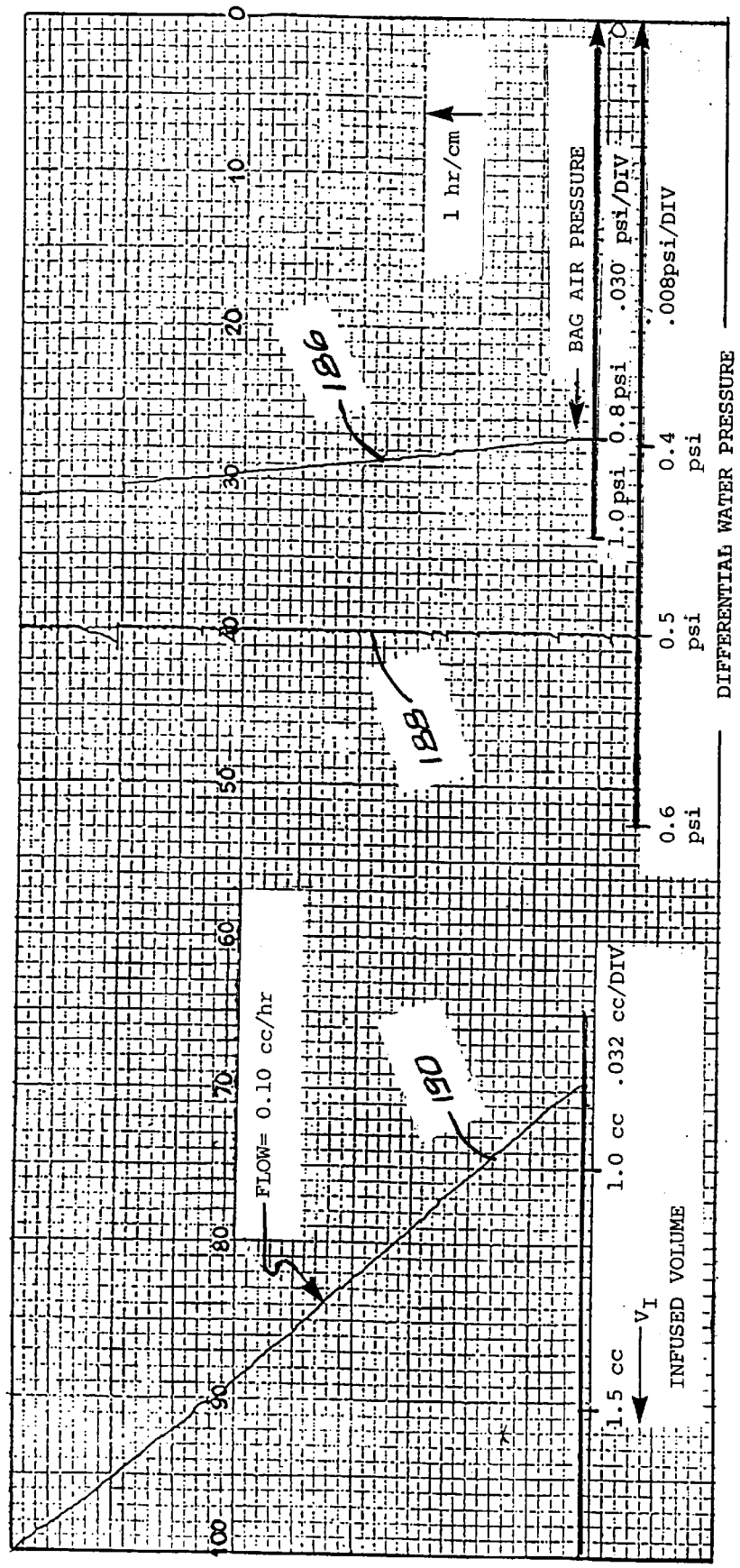
FIG. 7 shows a typical performance characteristic of the embodiment illustrated in FIG. 2.

FIG. 7 shows the performance of Type C-1 system as shown in FIG. 2. The back pressure downstream of check valve 70 was slowly increased tending to reduce the fluid flow rate. An incremental reduction in differential pressure across restrictions 36 causes an increase in air pressure applied to the flexible container 30 to maintain the differential pressure and, consequently, the fluid flow rate at the selected value. The increase in container air pressure is seen from curve 186, the constantcy of differential pressure is evident from curve 188 and the constancy of flow rate is seen from slope of the recording 190 of fluid volume that was transferred.

Figure 8:
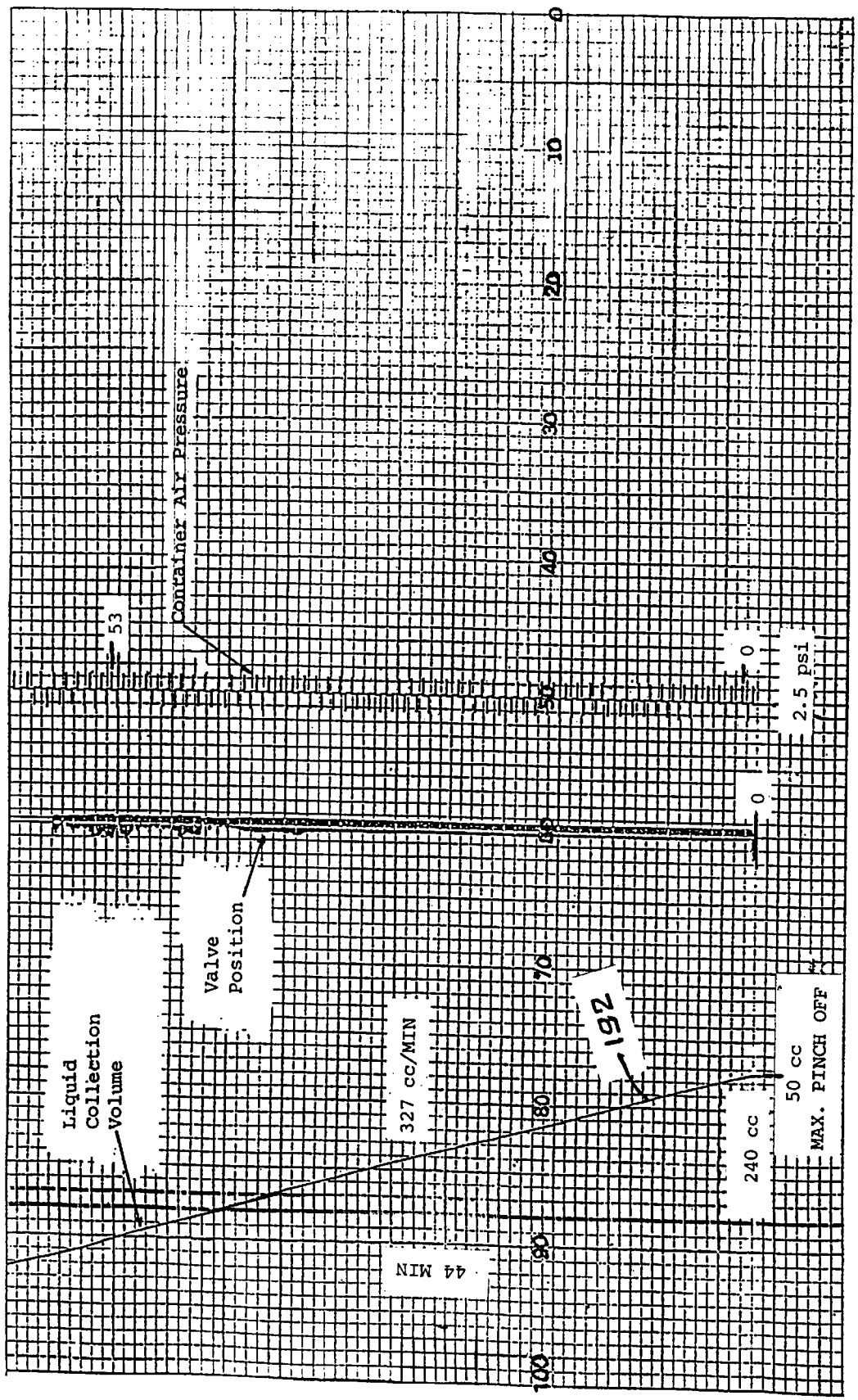
FIG. 8 shows a typical performance characteristic of the embodiment illustrated in FIG. 3.

FIG. 8 is a similar performance characteristic for a Type C system as illustrated in FIG. 3, showing the constancy of container air pressure maintained by the miniature pump 82 and the fluctuations of position of pinch valve 90 to maintain the fluid flow rate constant as seen by the constant slope of the recording 192 of the fluid volume that was transferred.

Figure 9:
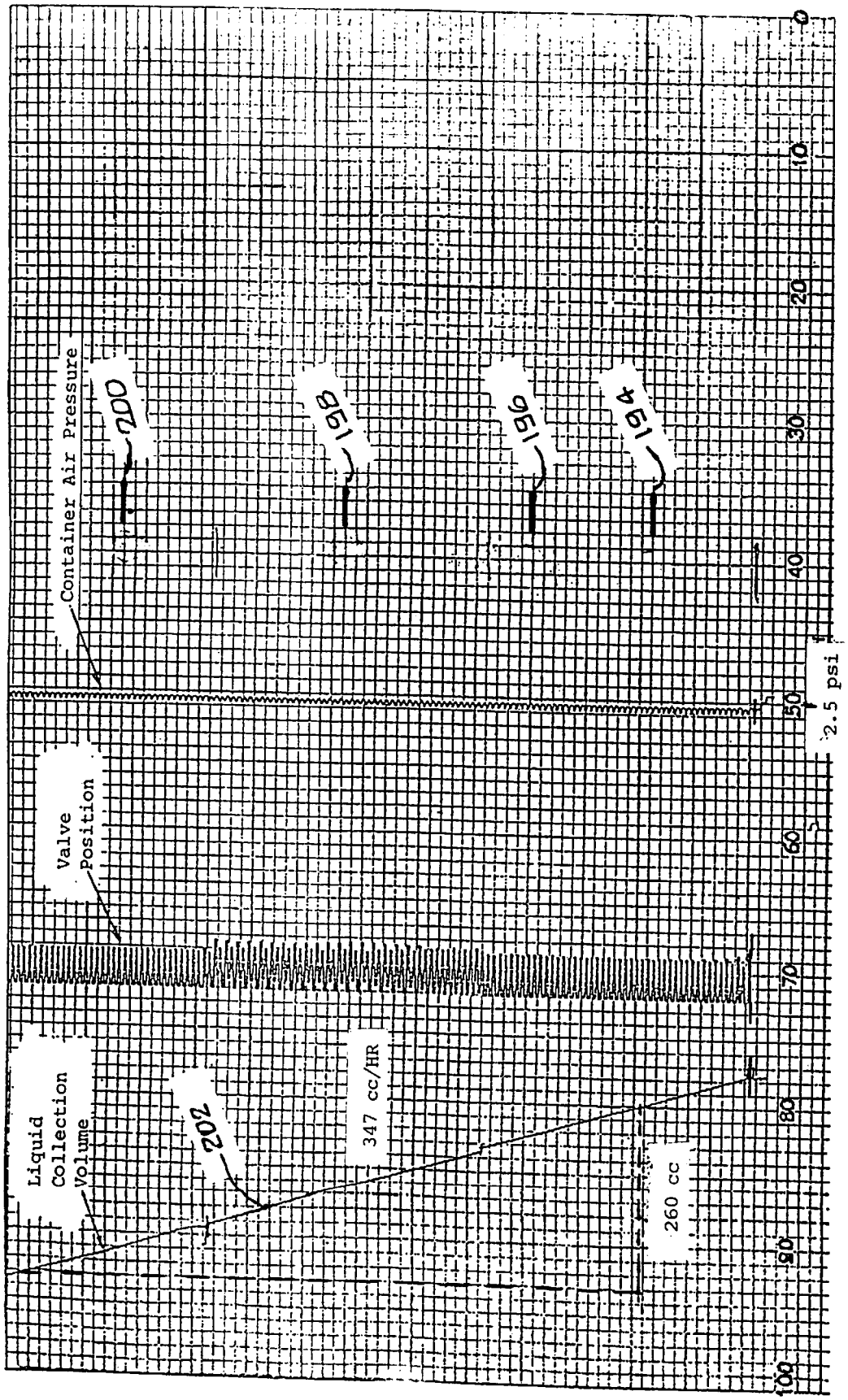
FIG. 9 shows a typical performance characteristic of the embodiment illustrated in FIG. 6 at various reservoir heights and orientations.

FIG. 9 shows conclusively that the performance of an embodiment of the invention is independent of height or orientation of the fluid container. At point 194 the container was in a vertical orientation at a height of 17 inches above the vessel. At point 196 the container was in a horizontal orientation at a height 17 inches above the vessel. At point 198 the container was in a vertical orientation at a height 44 inches above the vessel, and at point 200 the container was in a vertical orientation at a height 11 inches below the vessel. The constancy of fluid flow rate under all the changes in height and orientation is seen by the average slope of the recording 202 of the fluid volume that was transferred.

During an intravenous infusion it is frequently necessary to add one or more drugs for varying periods time. This can be accomplished readily with the subject invention with a single flow controller by the addition of one of more pressurizable reservoirs and measuring devices. A system for the simultaneous controlled transfer of two fluids between two pressurizable reservoirs, and the vessel is shown in the block diagram of FIG. 10, which is an expansion of the general diagram for a single fluid in FIG. 1.

Figure 10:
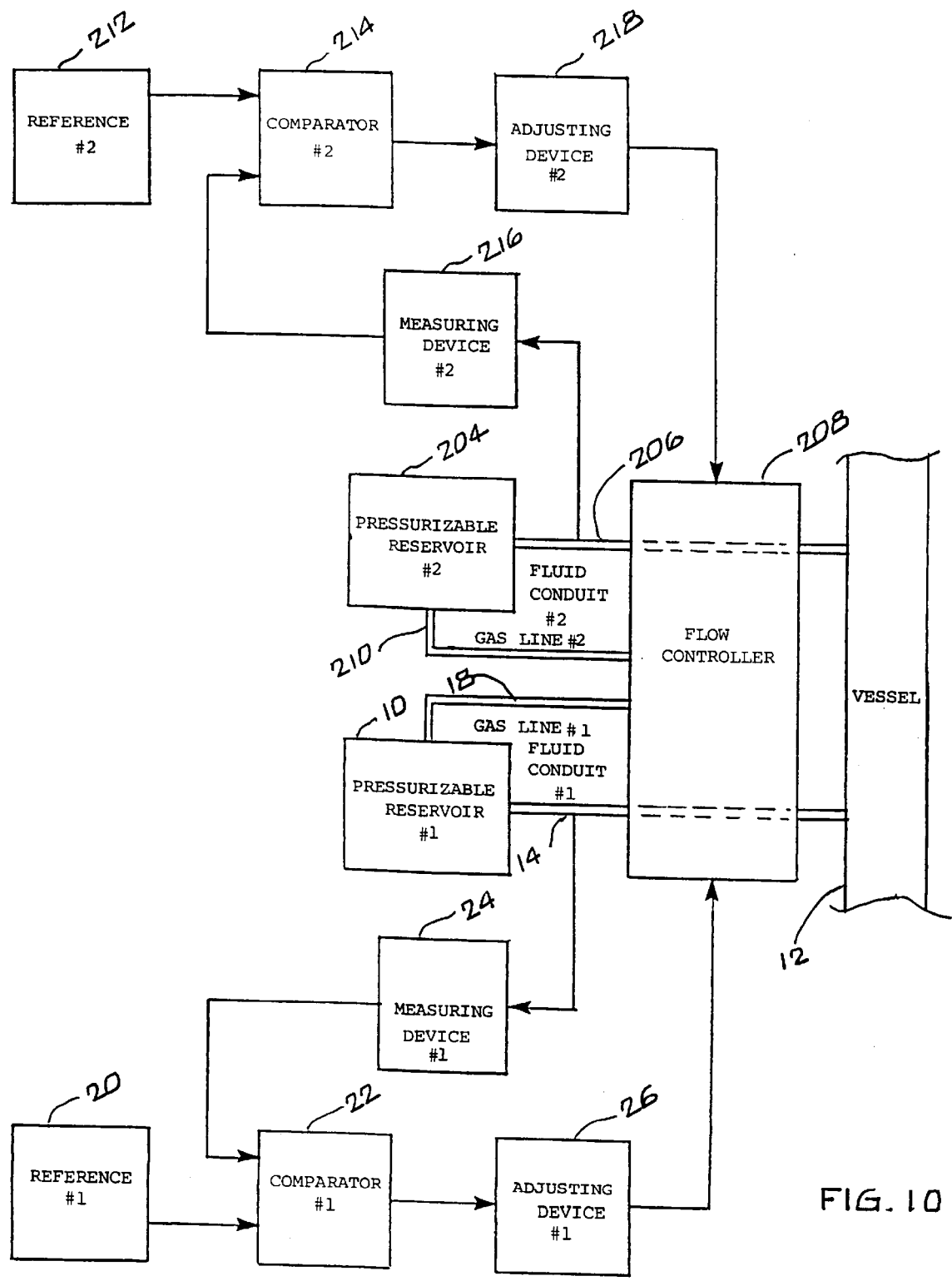
FIG. 10 is a functional block diagram illustrating expansion of the basic system for the transfer of two fluids under control of the same flow control means.

In addition to the components of a system for the transfer of a first fluid between a first pressurizable reservoir 10 and a vessel 12, that is shown in FIG. 1, the controlled fluid transfer system shown in FIG. 10 includes a second pressurizable reservoir 204 to contain a quantity of a second fluid, a second conduit 206 connected at one end to reservoir 204 and at the other end to the vessel 12 to transfer the second fluid between reservoir 204 and the vessel. Flow controller 208 applies gas pressure in a positive or negative sense with respect to atmospheric pressure through line 210 to reservoir 204 to provide a pressure difference between the reservoir and the vessel that will cause fluid to flow through conduit 206 between reservoir 204 and the vessel in a direction and at rate dependent on the sense and the magnitude of the pressure difference, as well as applying gas pressure through line 18 to reservoir 10 to cause a similar effect. Flow controller 208 may also include adjustable valve means, interactive with conduit 206 to vary the resistance to flow, and, thereby, the rate of fluid flow between reservoir 204 and vessel 12. A second reference means 212, provides an output related to the magnitude and sense of a selectable value of the second flow-rated parameter to a second comparator 214. A second measuring device 216 detects the second flow-related parameter and provides on output related in magnitude and sense to the second flow-related parameter to comparator 214. Comparator 214 provides an output related to the difference between the outputs of reference means 212 and measuring device 216 to a second adjusting device 218 which adjusts flow controller 208, including pressurization of second reservoir 204 in a direction and with a magnitude to provide the selected value of the second flow-related parameter. The selected value could be of any of several parameters related to the flow of the second fluid, such as the fluid flow rate in conduit 206, the change of volume of the second fluid in reservoir 204, or a pressure or pressure difference. It is to be understood, also, that the diagram of FIG. 10 shows the transfer of two fluids as an illustration of the transfer of multiple fluids under the control of a single flow controller with a single pressurizing means. More than two fluids can be so transferred.

Figure 11:
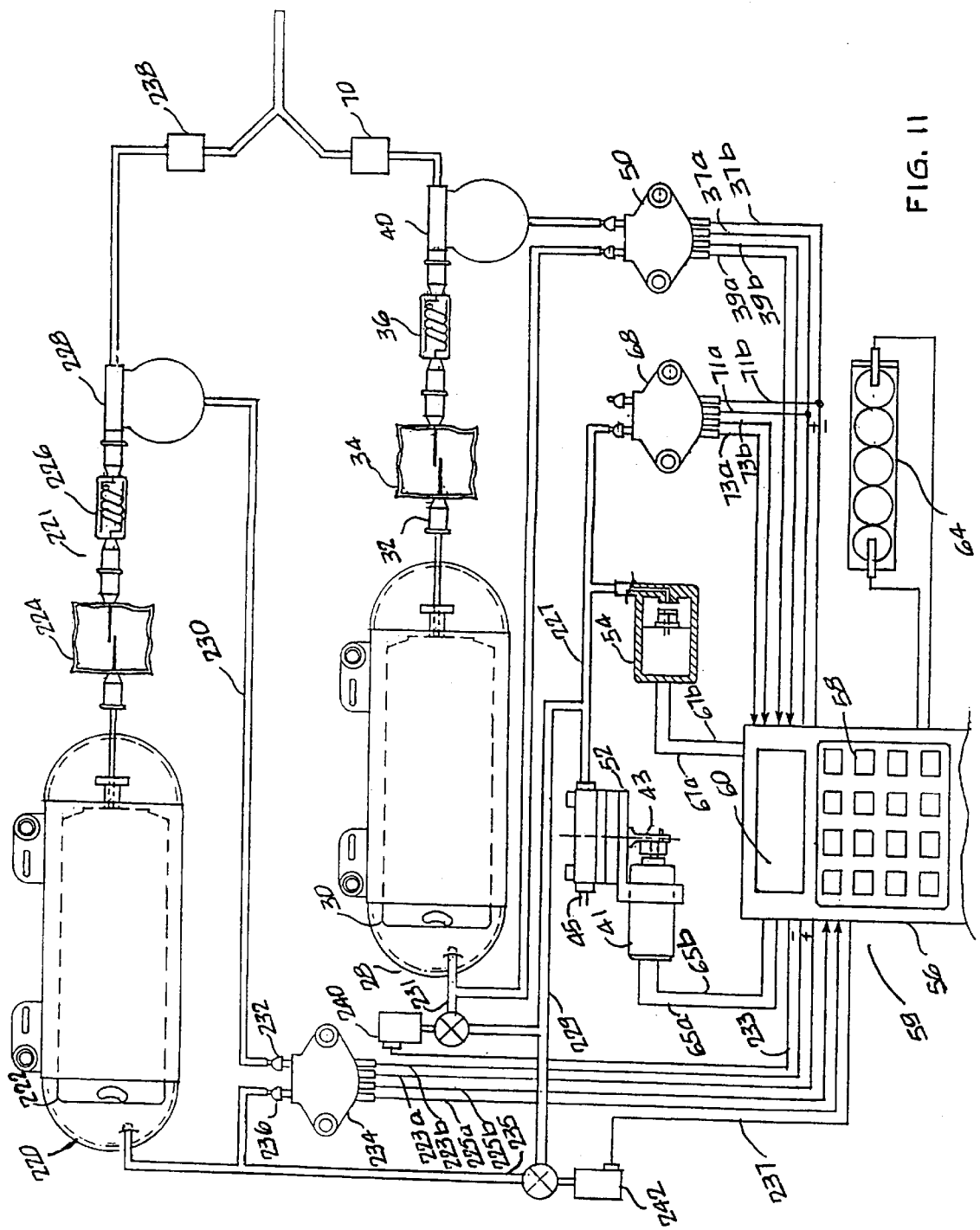
FIG. 11 is a schematic diagram of the embodiment shown in FIG. 10.

FIG. 11 is a schematic diagram of a Type C-1 system, similar to that of FIG. 2 but expanded, as shown in the block diagram of FIG. 10, for the transfer of two separate fluids. In addition to the components for the transfer of a first fluid shown in FIG. 2, and previously explained, the system in FIG. 10 includes a second pressure cuff 220, enclosing a conventional bag 222 filled with a second infusion fluid. The outlet of the second infusion fluid bag 222 is connected to a second integral intra-venous tubing set 221, which includes universal air trap 224, capillary flow sensor 226 and downstream isolating pressure tap 228, which is identical to isolating pressure tap 40. The pressure of the second infusion fluid downstream of capillary flow sensor 226 is transmitted through a flexible membrane in isolating pressure tap 228 to small bore line 230 and to the low pressure tap 232 of a second differential pressure transducer 234.

Flow of the second infusion fluid is controlled by the output from the second differential pressure transducer 234, which includes a resistive bridge that is excited by a voltage from electronic module 59 through leads 223a and 223b, and which provides an output related to the differential pressure across capillary flow sensor 226 to electronic module 59, through leads 225a and 225b. This signal is fed back and compared with the selected value for flow of the second infusion fluid stored in the computer, when then causes DC motor 41 of air pump 52 to be energized through leads 65a and 65b or solenoid valve 54 to be energized through leads 67a and 67b, as required, to maintain the output of the differential pressure transducer 234 at the control point.

As stated previously, the transmembrane pressure difference between the pressurizing air in cuff 220 and the second infusion fluid in bag 222, and, also, the pressure drop across the second air trap 224 are very small, so that for the high resistance type of capillary flow sensor 226, the air pressure can be fed to the high pressure tap 236 of differential pressure transducer 234 with little effect on accuracy, eliminating the need for an upstream isolating pressure tap, similar to tap 38 shown in FIG. 2. Check valve 238, as well as check valve 70, prevent reverse flow of fluid into either infusion fluid bag, which could be caused by differences in elevation between the bags or between either bag and the vessel. Air pressure is applied to cuff 28 from miniature pump 52, or air is exhausted by solenoid valve 54 through lines 227, 229 and 231 by actuation of solenoid valve 240, under the control of microcomputer 56 in electronic module 59 through lead 233. Similarly, air pressure in cuff 220 is increased from pump 52 or decreased by solenoid valve 54 through lines 227, 229 and 235, by actuation of solenoid valve 242 under the control of microcomputer 56 in electronic module 59 through lead 237.

Since continuous pressurization of either bag cannot take place without addition of a second pump and a second relief solenoid valve, operations of the pump 52 and valve 54 are time shared between the two pressure cuffs, 28 and 220. The time sharing can be on a scheduled basis or a demand basis. For example, a maximum specified delivery of infusion fluid of 1,000 ml in one hour at 350 mm Hg could be accomplished in 60 pressurization periods of 6 seconds each at a volumetric air flow rate of 167 ml/min (referred to 350 mm Hg). This is a 10% duty cycle, which means that, with continuous operation of the pump, ten intravenous fluid bags could each deliver 1,000 ml of fluid in one hour through sequential pressurization by a single pump. Alternatively, the pressurization period for any bag could be triggered by a drop in pressure corresponding to a decrease in a fluid volume of 16.7 ml (1.67% of a 1,000 ml initial fluid volume). Sampling of cuff pressures by gauge pressure transducer 68 through actuation of the cuff connection solenoid valves (e.g. 240, 242, etc.), could be performed at one second intervals. Since the actuation times of small solenoid valves and typically in a range of 5 to 10 milliseconds, and a transducer response of one millisecond is typical, the sampling period itself could be 100 milliseconds or less. A hierarchy of cuff pressurization sequencing should be established to take into account the possibility of simultaneous triggering.

A commercial DC motor-driven diaphragm pump is available that provides a flow rate of 250 standard ml/min at a pressure of 350 mm Hg, which corresponds to 171 ml/min at a pressure of 350 mg Hg, more than enough to supply 1,000 ml in one hour of 10 fluids from 10 sequentially pressurized IV bags. The pump weighs 1.5 oz.

In practice, the simultaneous infusion of as many as ten separate fluid mixtures would be rare, but the infusion of one to three or four fluid drug mixtures for limited periods in addition to the primary intravenous infusion fluid would not be uncommon. With existing multi-channel positive displacement peristaltic or cassette type of infusion pumps having a single drive, the flow rate of additional fluids is determined by the tubing size or size of the cassette used for each additional channel, and these are not easily changed or infusion selectively terminated. In the multi-fluid embodiment explained by FIG. 11, the desired flow rate for each infusion fluid is entered into the computer, as previously explained for the single fluid system of FIG. 2. Each fluid to be infused requires a separate bag, infusion cuff, restrictor and restrictor pressure drop transducer. The flow rate, infused volume, length and frequency of period of infusion for each fluid are individually entered into the keyboard and controlled by the computer, and those can be charged at any time by appropriate keyboard entries.

As important factor is the susceptibility of the pressurized system to air being drawn into the fluid transfer line. For a Type C-1 system for which conventional IV fluid bags might be used, such as those illustrated in FIGS. 2 and 11, this problem has been addressed, because some commercial IV fluid bags are supplied with a significant amount of air, as well as infusion liquid, sealed within the bag. In addition, air bubbles frequently can be noted to be clinging to the wall of the bag. Although it is feasible to supply bags that are completely liquid-filled, and, if necessary, de-gassed, it is desirable that the system be easily usable with conventional IV fluid bags that are commercially available. For this reason, means for removal of excessive air from the IV fluid bags, as well as for the prevention of air entry into the line, have been specified.

To remove air from the bag the IV bag tubing set can be supplied with a branch just past the IV bag outlet, terminating in a vent that will pass gas but becomes permanently sealed after having contract with a liquid. The vent can be made of a membrane filter that swells in contact with liquid, or a porous self-sealing polyethylene plug supplied by Porex Technologies of Fairburn, Ga. The bag is positioned vertically, so that the residual air in the bag accumulates at the bag outlet at the top; the fluid transfer line downstream of the branch is clamped shut: the branch line is unobstructed; and air pressure is applied to the cuff into pressurize the IV bag, forcing the air through the branch line and the vent. When all of the air has been forced through the vent, the infusion liquid will be forced against the vent permanently sealing it. The clamp on the fluid transfer line is opened, and the system is now placed in operation, with the IV bag and cuff oriented in any convenient position. As a precaution, the branch line can then be clamped shut.

Although it was not observed that any air remained, or that minute bubbles adhering to the inner wall of the IV bag broke free and passed into the fluid transfer line, there is no theoretical reason or experience that indicates that this cannot happen. It is considered prudent, therefore, to provide the option of including an air trap in the fluid transfer line at the outlet of the IV bag.

For an inverted IV bag or bottle in a gravity feed, the air accumulates at the top end, opposite to the outlet port. Any air that might find its way out of the bag would be trapped in the drip chamber. For the non-gravity-dependent infusion system the bag could be oriented in any position, and any residual air retained in the bag could conceivably find its way out, particularly if the bag is positioned vertically, with the outlet at the top. A drip chamber could be effectively hung vertically, with the outlet at the bottom, as for a gravity feed, but this is contrary to the objective of the non-gravity-dependent system.

Figure 13:
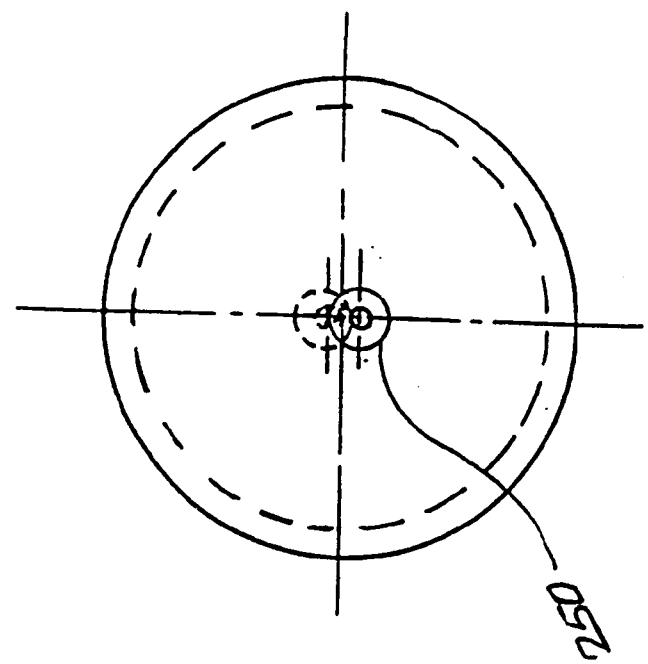
FIG. 13 is an end view of the air trap shown in FIG. 12.
Figure 12:
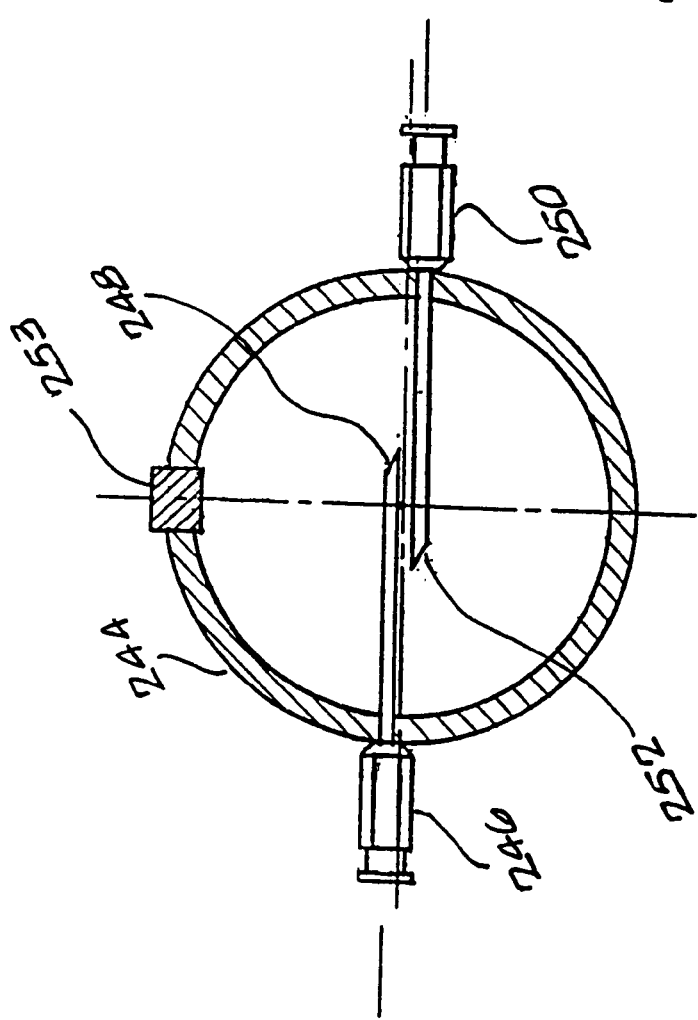
FIG. 12 is a sectional view of a universal omni-directional air trap similar to one disclosed in FIG. 2.

A drawing of a novel universal air trap design is shown in FIGS. 12 and 13. This trap will accumulate air not to exceed a certain volume (determined by the trap size and geometry), in any position or orientation, without permitting the air to pass into the liquid outlet. The universal trap consists of a chamber 244 with an inlet tube 246 having an outlet 248, and an outlet tube 250 having an inlet 252, in another side, the outlet tube overlapping the inlet tube. In the preferred design shown in FIGS. 12 and 13, the chamber is spherical, having an axis. The inlet tube is a hypodermic needle protruding through the chamber wall, and coaxial with the cylinder axis. The outlet tube is a hypodermic needle protruding through the opposite wall, and also coaxial with the cylinder axis. The axes of the two tubes are displaced by an amount that is small compared to the spherical diameter of the interior of the chamber. The volumes above the inlet and the outlet tubes are approximately equivalent in any orientation. It is to be noted that either tube in the design of FIGS. 12 and 13 can be the inlet, and the other the outlet. The maximum volume of air that can be accumulated is defined by a liquid volume where the inlet of the outlet tube is completely covered by liquid.

The universal air trap will be supplied as a disposable element in a sterile package, but it will be filled with air. As shown in FIG. 12, a porous vent 253 made of a material that becomes permanently sealed after liquid contact, is located in the wall of the chamber 244 along an axis that is orthogonal to the flow axis. The air trap is oriented temporarily with the flow axis horizontal, and the air in the IV bag, as well as that initially in the chamber, is removed by the same procedure as that described above, except that a branch is no longer needed.

The universal air traps 34 and 224 shown in FIGS. 2 and 11 have features similar to the embodiment of FIGS. 12 and 13 in that the inlet and outlet needles overlap at the center so that approximately half of the initial volume of liquid would need to be displaced by air before any air could enter the fluid transfer line. The essential difference is that, in place of a chamber with rigid walls, a flat bag with flexible but relatively non-distensible walls is provided. The disposable bag is supplied in an evacuated condition, so that air removal from the bag is not required. With the fluid transfer line clamped, the fluid in the pressurizable container is pressurized, and the bag fills with liquid until it is fully expanded, at which point the clamp can be removed from the fluid transfer line. Air in the IV bag must still be removed, however, and for this, a branch line with a self-sealing, liquid-blocking plug is suitable, as explained above.

The procedure for air removal from a commercial IV bag and use of the universal air trap make it unlikely that any air bubble will pass into the line downstream of the air trap. Unlike the situation with positive displacement pumps, where the pump inlet could be under negative pressure (e.g. if there is no gravity feed, or if the gravity line from an elevated IV fluid container is partially occluded), all sections of the IV container and line of the non-gravity-dependent infusion system are under positive pressure, so that air cannot be ingested into the line through a leak. Nonetheless, to guard against the possibility of a retained air bubble passing through the line, a concept is herein disclosed for a novel air-in-line detector.

It is possible to use the capillary restrictor of the differential pressure flow sensor as an air-in-line detector, under the premise that the fluid resistances for air and liquid would be different. This is still a feasible method, but a fluid resistive bridge may be required, increasing the line resistance; and, also, the effect of a small air bubble could be difficult to detect, since the low pressure drop across the restrictor caused by an air bubble could be confused with a low pressure drop caused by a low selected flow rate or an accidental occlusion. A superior method has been devised in which change of electrical impedance of the IV solution between two electrodes in the line is measured. Infusion solutions are electrically conductive to a reasonably high degree compared to air, which is non-conductive (at low voltages), and this property can be used in a simple and inexpensive air-in-line detector. A laboratory model of such a detector has been tested with positive results.

Figure 14:
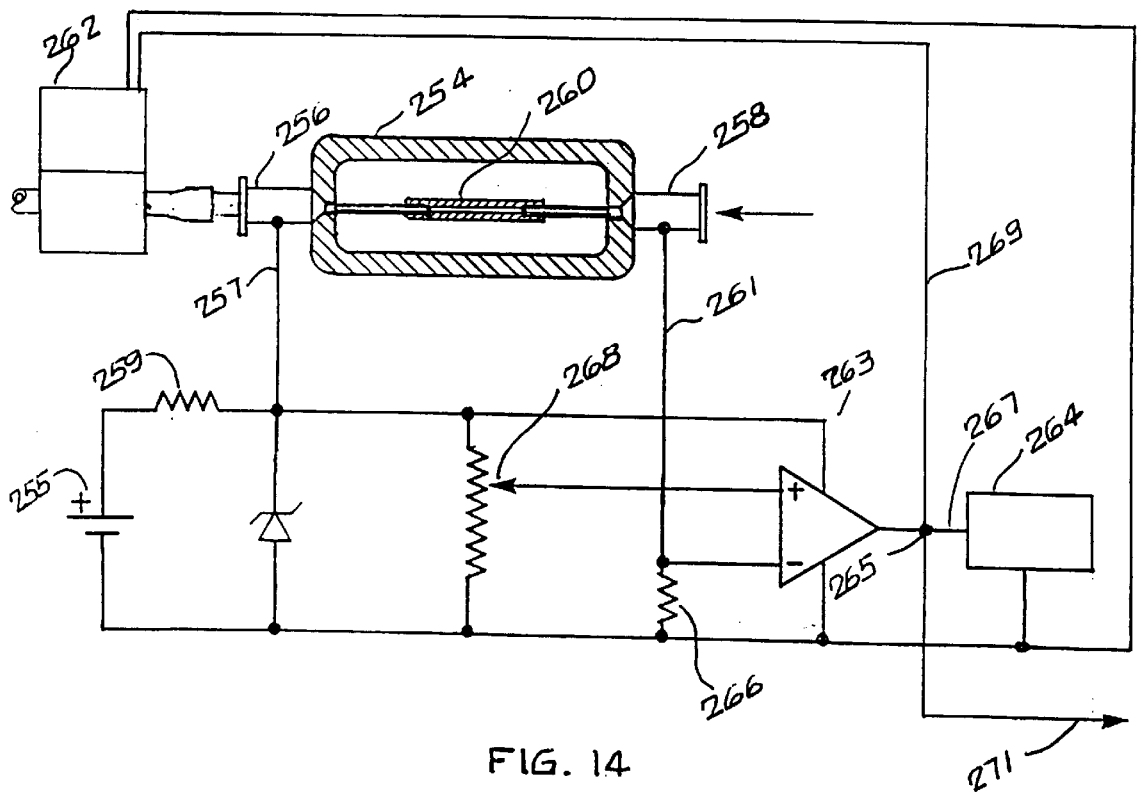
FIG. 14 is a schematic diagram of a novel gas-in-line sensor.

A simple embodiment of an electrical impedance type of air-in-line sensor is shown in FIG. 14. A non-conductive housing 254 contains a conductive inlet hollow needle 256 and a conductive outlet hollow needle 258. The needles are joined by a non-conductive tube 260. The IV liquid flows through both needles and the joining tube, and the IV liquid provides an electrically conductive path between the two needles. When an air bubble enters the non-conductive tube, the conductivity is drastically reduced, and this change in conductivity is detected in an external circuit to cause interruption of flow by actuation of an in-line pinch valve 262 and through lead 271) solenoid valve 54 of FIGS. 2 and 11 and, also, actuation of an alarm 264.

Referring to the circuit of FIG. 14, conductive needle 256 is connected to a positive voltage from a DC supply 255, through lead 257 and resistor 259, and conductive needle 258 is connected to a negative voltage from a DC supply through lead 261 and resistor 266, causing a very low electrical current to be passed through the liquid in the non-conductive tube 260. The electrical contact to the liquid is made through the input and output needles 256 and 258, and the resulting current develops a voltage across resistor 266 at the input to a comparator 263 with a threshold reference voltage that is selected by adjustment of a potentiometer 268. If the voltage thus developed across resistor 266 at the comparator input exceeds the reference threshold, signifying relatively high conductivity due to the absence of air bubbles in the line, then the comparator output 265 can provide a logic state representing "alarm off."

Conversely, at such point that one or more air bubbles enter the line, the available cross-sectional area of conductive liquid instantly becomes minimal, the comparator input voltage falls to a value below the threshold, and a signal is provided from the comparator output 265 to the alarm 264, through lead 267 and to the shut-off valve 262, through lead 269, and the pressure dump valve 54 (FIGS. 2 and 11) through lead 271 to stop further flow of infusate. Alarm 264 could include an audible tone and a flashing red LED, and valve 262 could be motor-driven pinch valve or a solenoid-actuated pinch valve.

In laboratory tests, very small bubbles produced very large changes in conductivity, due, partly, to the small bore of the non-conductive tube 260 that was used. Such large changes, exceeding a ratio of 100:1, are easily detected. One threshold setting may perform reliably for a large variety of IV solutions, perhaps for all standard solutions in use. However, a switched threshold control, with a few settings for all known solutions is also feasible.

In the laboratory tests measurements were made with several test solutions, including 5% dextrose and 0.9% sodium chloride. Conductivities as high as 0.5 micromhos were measured without air bubbles, and lower than 0.001 micromhos (the limit on the range of the test instrument used) with a bubble present. The conductivity in the presence of air is very low, but not zero, due to adherence of a liquid film on the wall of the non-conductive tube. The measured conductivity of the 5% dextrose solution was approximately half that of 0.9% sodium chloride solution. It is considered that the 5% dextrose solution is representative of the least conductive IV fluids that should be encountered.

In the tests that were conducted, 30 gauge hypodermic needles were used, spaced apart by a gap of 0.063 in., and the non-conductive tube was a section of plastic microbore tubing with an internal diameter of 0.010 in. The total volume within the non-conductive section was less than 0.1 microliter. Air bubbles with a smaller volume could be detected.

A general requirement for infusion pumps is that they be capable for detecting air bubbles of 0.5 ml, and that upon detection, the flow should be stopped and an alarm actuated before the bubbles can reach the patient. Detection of smaller bubbles is required for neonates and arterial line infusions. Some commercial infusion pumps apparently can detect small air bubbles, on the order of 0.01 to 0.15 ml (10 to 150 microliters). It is seen that the electrical conductivity air-in-line detector can be considerably more sensitive, since in the initial tests, 0.1 microliter bubbles and smaller were detected. The sensitivity can be decreased to sense only larger air volumes by increasing the volume (e.g. diameter, length or both) of the non-conductive tube or by timing the period of low conductivity when air is present.

The question of electrical safety of an electrical impedance type of air-in-line detector must be addressed, since a conductive pathway into the body is introduced by the IV fluid. Patients are not considered to be electrically susceptible during peripheral venous infusion, but they could be susceptible when undergoing central venous infusion, which is generally the case during hyperalimentation. The excitation voltage for the electrical impedance air detector shown in FIG. 14 should be low, typically on the order of 6V DC or lower. At this voltage, current through a 12 inch catheter filled with hyperalimentation solution, would be under 15 microamperes. For additional safety, the excitation supply for the electrodes should be isolated from the main rechargeable battery of the infusion device. The excitation current for the electrical impedance air detector will be on the order of a few microamperes, so that a disposable small high-energy density battery, such as a lithium cell, can be used, as a separate excitation supply, providing a long duration of operation. Since this battery is not rechargeable, there will be no connection to a charger or to any other external circuit.

The electrical leads to the needle electrodes can be sealed and insulated to avoid any external pathway by inadvertent contact of a conductive element. For ultimate security the separate battery for the electrical impedance air detector can be encapsulated with a current-limiting resistor, which will prevent the current from exceeding a safe low value.

The features and advantages of the electrical impedance air-in-line detector are:

a) It is simple and reliable.

b) It is inexpensive.

c) It can be used with opaque, colored and transparent fluids.

d) The sensing element is sterile and disposable.

e) For the pressurized, non-gravity-dependent infusion system, the sensing element can be combined with the capillary flow sensing restrictor in a single disposable component.

In prior air-in-line detectors, the size of the air bubble detected depends on the inner diameter of the flow tube that is monitored. Interruption of a beam of light of ultrasound that is transmitted transverse to the flow path from a source on the exterior of the tube is detected as an indication of passage of an air bubble. For unambiguous detection, the bubble should fill the lumen of the tube. Thus, in one commercial device for detection of bubbles in the blood lines, by use of a light beam, the minimum size of bubble that can be detected in a line having a 0.25 in inner diameter is 0.5 ml, and in a 0.375 ID line, the minimum detectable bubble size is 1 ml. In another commercial air-in-line detector, that uses a beam of ultrasound, the bubble also must fill the inner diameter of the tube for detection. Thus, for a tube with an inner diameter of 0.125 inches, the minimum detectable bubble size is 0.015 ml, which is the size of a spherical bubble with a diameter of 0.125 inches. In the new electrical impedance bubble detector, the diameter of the minimum size of detectable air bubble in relation to the inner diameter of the flow tube depends on the minimum detectable change of electrical impedance between the electrodes. For an embodiment such as that shown in FIG. 14, where the impedance is purely resistive and the circuit is excited by direct current, the ratio of electrical resistance that is measured between the electrodes and the resistance of a tube completely filled with infusate, is related to the volume occupied by a bubble between the electrodes. For example, for a condition where a single air bubble exists in the flow tube between the electrodes, let $D_T$=inner diameter of the tube, $D_B$=the bubble diameter, $r_B$=ratio of bubble to tube diameters, $D_B/D_T$; $R_T$=electrical resistance between electrodes of a totally liquid filled tube; R'=electrical resistance between the electrodes with a bubble present; $V_T$=volume of the tube between the electrodes, $V_B$=volume of the bubble between the electrodes, the relations are as shown in Table II.

TABLE II

RELATIONSHIPS BETWEEN DIAMETERS AND VOLUMES OF GAS BUBBLES AND ELECTRICAL RESISTANCES BETWEEN ELECTRODES IN A TUBE FILLED WITH A CONDUCTIVE LIQUID

| $r_B$ | $R'/R_T$ | $V_B/V_T$ |
|---|---|---|
| 1.0 | →∞ | 1.0 |
| 0.8 | 2.42 | 0.51 |
| 0.5 | 1.17 | 0.125 |
| 0.33 | 1.05 | 0.037 |
| 0.25 | 1.02 | 0.0156 |

Thus, if the sensitivity of the inter-electrode resistance measuring circuit is 2, the minimum size of detectable bubble is ¼ the inner diameter of the tube and 1/64 the volume of a bubble that completely fills the lumen of the tube. For a 0.125 in. ID tube, the minimum detectable air bubble volume is 0.25 microliters. For a circuit sensitivity of 5%, the minimum detectable air bubble volume is 0.6 microliters. This is over an order of magnitude smaller than the minimum size of bubble that can be detected by available infusion pumps, and the detectable volume can be made smaller by reducing the internal diameter of the tube.

Figure 15:
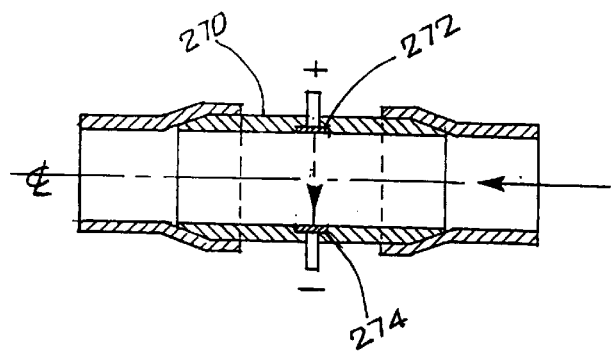
FIG. 15 is a variation of the gas-in-line sensor shown in FIG. 14.

In the means for detecting the presence of a gas in an electrically conductive liquid flowing through a line shown in FIG. 14, the line includes a section 260 with a relatively non-conductive wall, a longitudinal axis and an interior surface in contact with the electrically conductive liquid, and electrodes 256 and 258 that are spaced apart on the longitudinal axis and connected to the electrically conductive liquid. It is preferable, but not essential, for the electrodes to be spaced apart on the longitudinal axis, for flexibility in selecting a value of electrical resistance between the electrodes. The system is also operative in the arrangement shown in FIG. 15, which shows means for detecting the presence of a gas in an electrically conductive liquid flowing through a line including a section 270 with a relatively non-conductive wall, a longitudinal axis and an interior surface in contact with the electrically conductive liquid and electrodes 272 and 274 that are connected to the electrically conductive liquid and that are located in the same plane transverse to the longitudinal axis.

For an intravenous infusion device, the flow rates of the infusion fluid are relatively low (e.g. 17 ml/min or less), so the small bore infusion tubing can be used without introducing an excessive pressure drop. This is advantageous for maintaining a reasonable fluid velocity and detecting small gas bubbles even if they fill the entire lumen of the flow tube. For extracorporeal blood flow, the flow rates are considerably higher, in the region of 5 to 8 liters/min, so that the interior diameter of the flow tube can be much larger than for intravenous infusion. The minimum size of gas bubble detected for blood flow can be reduced by decreasing the diameter of the flow tube at the bubble detecting section. If the section does not have a smooth contour, there could be excessive pressure loss and eddy formation causing hemolysis. The embodiment shown in FIGS. 16 and 17 show means to reduce the diameter of the gas bubble detection section with minimum pressure loss or hemolysis by configuring the section as a venturi. As shown in FIG. 16 axially spaced electrodes 276 and 278 are placed in the elongated throat 280 of the venturi. The inlet 282 is well rounded, and the divergent outlet 284 has an included angle of 20 degrees. The inlet diameter is 0.375 in., and the ratio of throat to inlet diameters is 0.5. the gas volume to completely fill the throat is 0.057 ml, which is ⅛ that to completely fill the 0.375 dia.

inlet tube. The coefficient of discharge is typically 98%, so that pressure loss is minimal, as is eddy formation and hemolysis. The lower pressure in the throat favors bubble detection by increasing the bubble volume, typically by 15% at a substantial flow rate of 6 lpm. Care must be taken that dissolved blood gases do not come out of solution at the throat to give a false indication. At a moderate inlet pressure of 120 mm Hg gas pressure, the throat pressure will be atmospheric. There will be a significant pressure drop across the infusion needles or catheter, so that a venturi type of gas bubble detector can be proportioned to increase sensitivity of bubble detection without interference by dissolved blood gases in the throat.

Another means of increasing sensitivity of bubble detection by reducing the diameter of the gas bubble detection section without a substantial increase in pressure loss or hemolysis is by using multiple parallel paths of smaller diameter, which is illustrated in the embodiment shown in FIGS. 18, 19 and 20. The gas presence detecting means includes a housing 286 with an inlet 288 and an outlet 290, and a plurality of relatively non-conductive conduits 292, 294, 296 and 298 between the inlet and the outlet. Each conduit has a pair of axially spaced electrodes 300, 302, 304 and 306. Conduits 292, 294, 296 and 298 are of smaller cross-section than the inlet and the outlet, but they are hydraulically connected in parallel, to maintain the same total flow area. Electrode pairs 300, 302, 304 and 306 are electrically connected in series with a voltage source so that a single bubble passing through any of the conduits will interrupt the circuit. As shown in FIGS. 18 and 19, four conduits, each with ½ the diameter and ¼ the flow area of the inlet and outlet, are connected in parallel to provide the same total flow area as those of the inlet 288 or the outlet 290. For the same dimensions of each bubble detection section and the inlet and outlet was the venturi detector of FIGS. 16 and 17, the multiple circuit detector in FIGS. 18 and 19 has lower sensitivity, because the total electrical path is longer and the total electrical resistance of the conductive liquid is greater. However, there is no reduction in absolute pressure and no risk of dissolved gases leaving solution at the detector section.

The construction shown in FIGS. 18, 19 and 20 is very inexpensive and compatible with a disposable element. Housing 286 is molded in two halves, 308 and 310, of a relatively non-conductive plastic, such as polystyrene or polycarbonate. Corresponding halves of each bubble detection conduit are molded in each housing half. The paris of electrodes are conductive pins that are molded as inerts into housing half 310. After molding, the two halves are bonded together to form the electrical impedance gas detection device.

Figure 21:
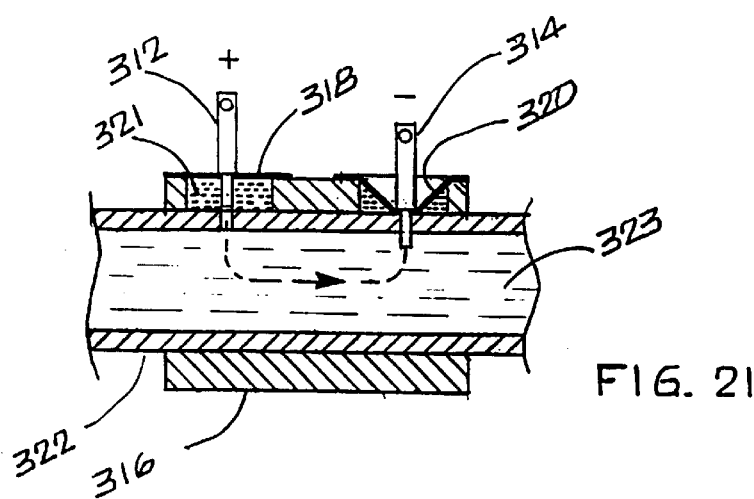
FIG. 21 is a diagram of yet another version of the sensors shown in FIGS. 14 and 16.

The gas detection devices described above are all configured as inexpensive disposable elements that must be inserted into a fluid transfer line, although they could, probably, be provided as integral members of disposable IV sets. Although the disclosed gas detection device could be most effective when provided as a separate component, there could be some advantage of providing a reusable sensing element that could be slipped over existing IV tubing. A limitation, here, is that a separate element may be required for each tubing size. FIG. 21 shows an element, including a non-conductive housing 316 that can be slipped over a section of infusion tubing. Two axially spaced-apart needles 312 and 314, that act as electrodes, are retained in housing 316 by diaphragms 318 and 320. The volume between each diaphragm and the outer surface of the tubing 322 is filled with a disinfectant gel 321. When the housing 316 is slipped over the tubing 322, the points of the needles are raised above the outer diameter of the housing. After the housing has been located, the needles are pressed into the tubing wall, where, after full insertion, they protrude into the interior of the tubing, making contact with the conductive liquid 323. The disinfectant gel is squeezed in contact with the needle and the housing, preventing infection past the needles, which also act to anchor the housing to the tubing. For illustration, FIG. 21 shows needle 312 raised before insertion, and needle 314 after insertion.

In the gas presence detectors described above, the change in conductive liquid resistance between two electrodes is measured and compared to a reference to indicate presence of a bubble. Changes in liquid conductivity that could be caused, for example, by changes in temperature, or addition of a second or third fluid during infusion could cause false indications of gas bubbles. Such an effect could be offset by providing temperature compensation for a reference, or storing the initial electrical output of a normal liquid filled section after fluid addition in a memory for use as a subsequent reference.

Figure 22:
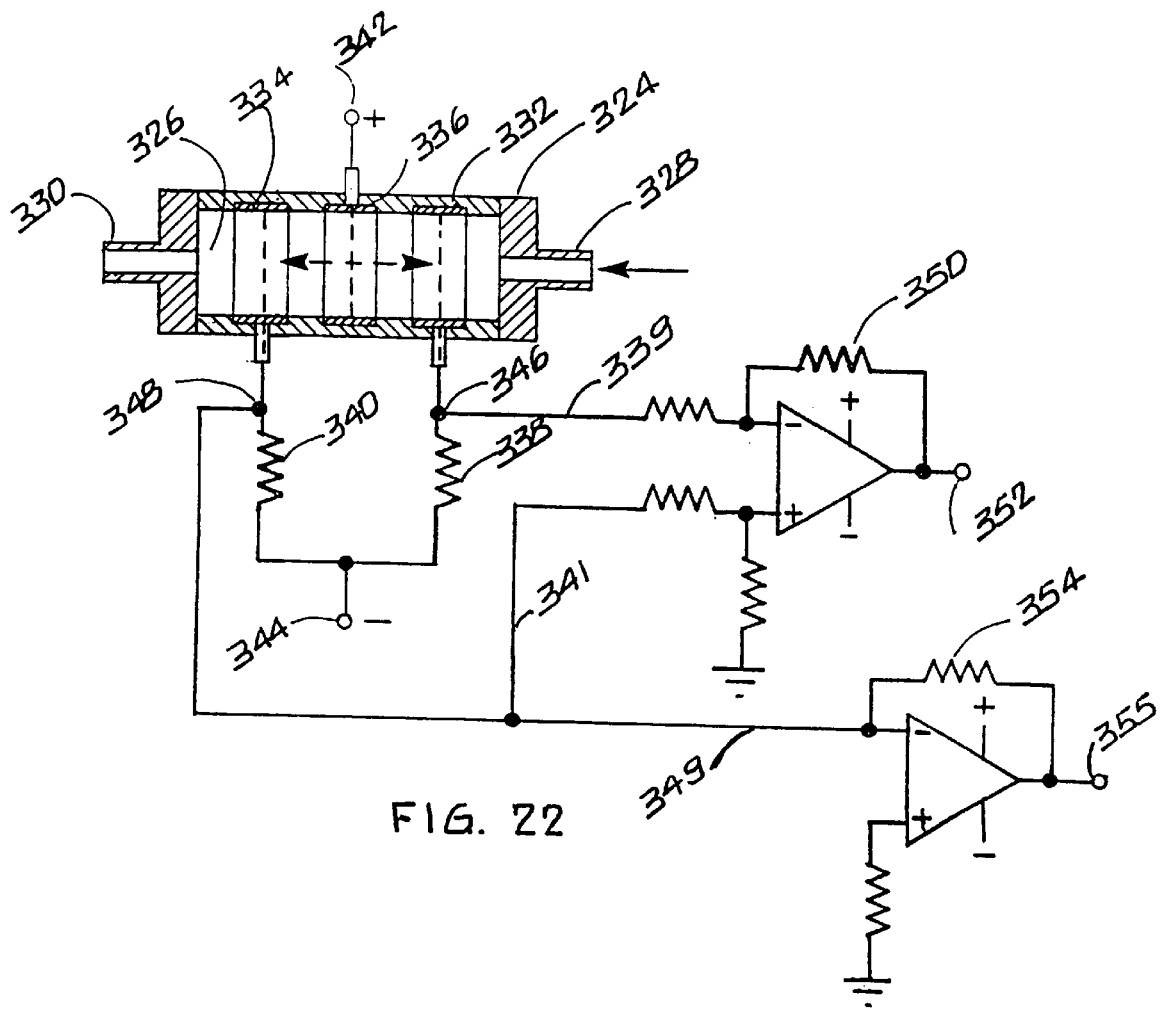
FIG. 22 is a diagram of a version of the sensors shown in FIGS. 14 and 16, illustrating bi-directional differential sensing.

Another embodiment that makes the gas presence detection independent of the liquid conductivity is shown in FIG. 22. This is a differential electrical impedance sensor, in which the impedance between an upstream pair of electrodes is compared with the impedance between a downstream pair of electrodes. The two impedances are compared in a bridge circuit, and an imbalance indicates passage of a gas bubble.

Referring to FIG. 22, the detector includes: a housing 324 made of relatively non-conductive materials, with an internal tubular chamber 326, having an inlet 328 and an outlet 330; an upstream conductive electrode, here shown as a ring 332 in the wall of the chamber 326 near the inlet 328; a downstream conductive electrode, here shown as a ring 334 in the wall of the chamber 326 near the outlet 330; and an intermediate conductive electrode, here shown as a ring 336 in the wall of the chamber 326 between the upstream electrode 332 and the downstream electrode 334. The resistances of the electrically conductive liquid between the intermediate electrode 336 and both the upstream and downstream electrodes 332 and 340 are connected with external resistors 338 and 340 in a bridge circuit between terminal 342, which is connected to a source of positive voltage, and terminal 344, which is connected to a source of negative voltage. The branch voltages at points 346 and 348 are fed through leads 339 and 341 to differential amplifier 350, whose output voltage at terminal 352 will be zero when no gas bubble is present, and the interelectrode resistances are equal, and which will swing in a positive direction when a gas bubble is present between the upstream electrode and the intermediate electrode. As described for the embodiment of FIG. 14, an output at terminal 352 can be used to actuate an alarm, a pinch valve on the fluid transfer tube, and a fluid container pressure dump valve. The voltage at point 348 is also fed through lead 349 to an operational amplifier 354, whose output voltage at terminal 355 is related to the conductivity of the liquid solution, which information is useful for verifying the composition of the liquid being infused. The outputs of amplifiers 350 and 354 can also be fed to a microcomputer, which can adjust the gain of the bridge circuit so as to provide a ratio of upstream and downstream interelectrode liquid resistances for the determination of bubble size, independent of the liquid conductivity.

Figures 23, 24:
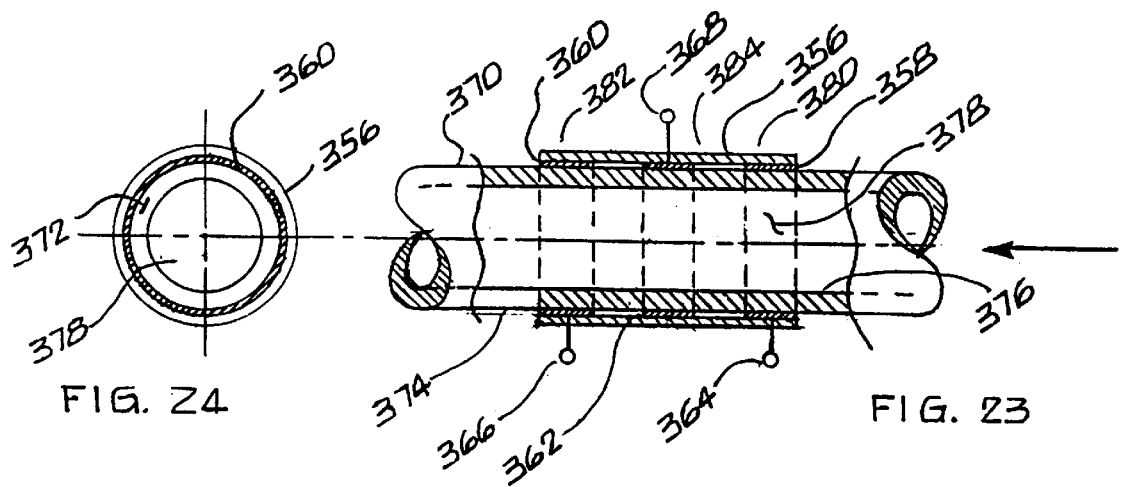
FIG. 23 is a sectional elevation view of a bi-directional differential sensor, similar to the sensor of FIG. 22, but using capacitive coupling.
FIG. 24 is an end view of the sensor shown in FIG. 23.

FIGS. 23 and 24 show an embodiment of means for detecting the presence of a gas in an electrically conductive liquid flowing through a line, in which the line includes a section with a relatively non-conductive wall and an interior surface in contact with the electrically conductive liquid, a pair of spaced-apart electrodes define a path for electrical current through the conductive liquid between them, the electrodes are separated from the interior surface by a thickness of the non-conductive wall and capacitively coupled through the wall to the electrically conductive liquid, and a source of electrical voltage with an alternating component, is connected to the electrodes in a manner to create a voltage difference and an electrical current flow in the conductive liquid between them.

As shown in FIGS. 23 and 24 the gas presence detector sensor assembly includes a tubular housing 356 made of relatively non-conductive material, an upstream conductive electrode 358, a downstream conductive electrode 360, and an intermediate conductive electrode 362 between the upstream and downstream electrodes, all three electrodes here shown as rings fastened to the interior of housing 356. Upstream electrode 358 is connected to an upstream external terminal 364; downstream electrode 360 is connected to a downstream external terminal 366; and intermediate electrode 362 is connected to an intermediate external electrode 368. The housing and electrode assembly is slipped over a section of a fluid transfer line 370 with a relatively non-conductive wall 372, an exterior surface 374 in intimate contact with the three electrodes, and an interior surface 376 in contact with the conductive liquid 378 flowing in the line. Each conductive electrode in contact with the exterior surface of the line, together with a corresponding section of the interior surface in contact with the conductive liquid, form plates of upstream coaxial capacitor 380, downstream coaxial capacitor 382 and intermediate coaxial capacitor 384 in which the non-conductive line wall is the dielectric. Terminal 368 is connected to a source of electrical voltage with an alternating component, and terminals 364 and 366 are connected to an external current sensing circuit.

Figure 25:
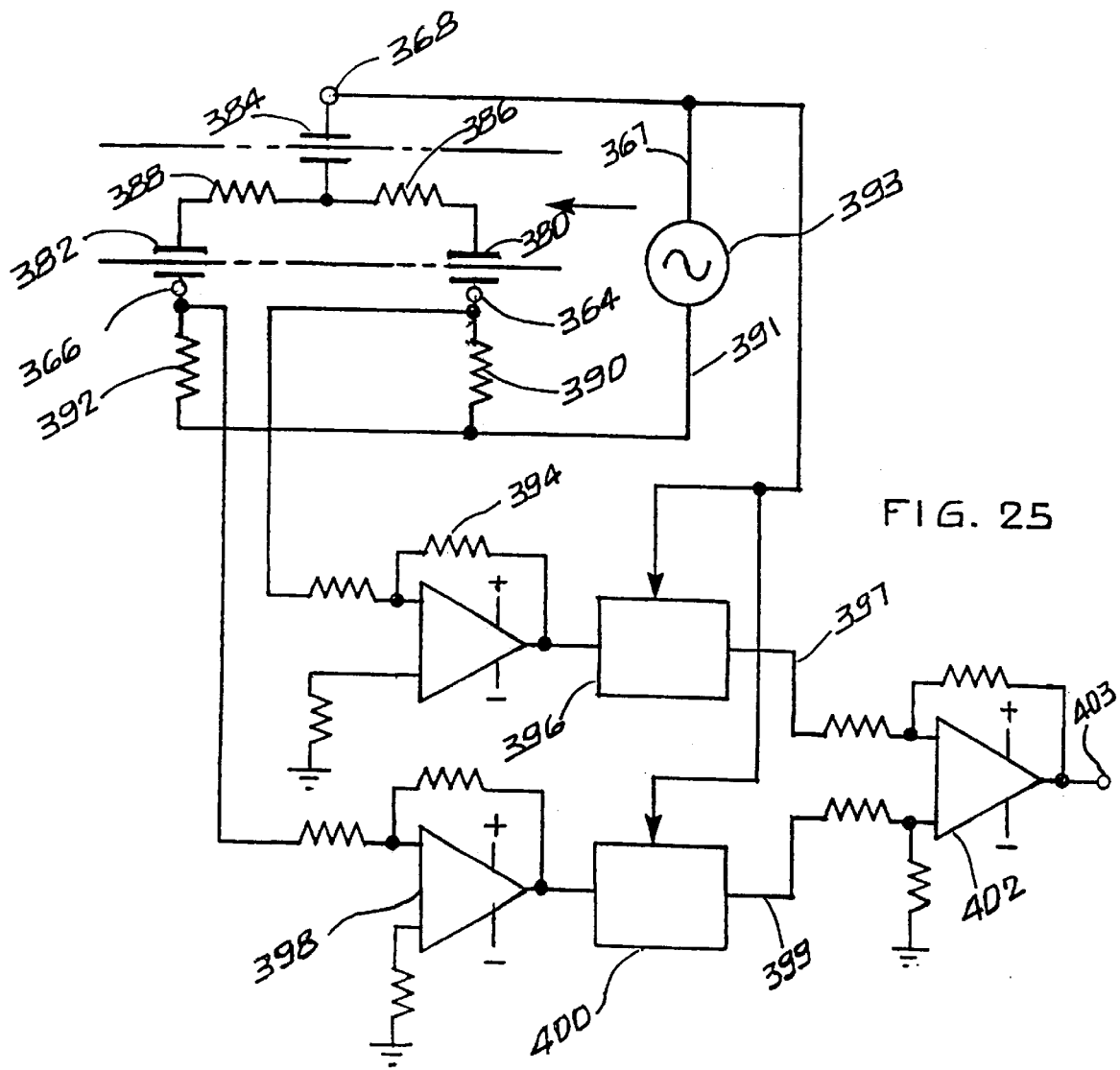
FIG. 25 is a schematic diagram of a gas-in-line sensing system using the sensor shown in FIGS. 23 and 24.

A schematic diagram of the capacitively coupled electrical impedance type of gas presence detector is shown in FIG. 25. The circuit is basically a capacitvely coupled resistive bridge, consisting of the upstream resistance 386 of the conductive liquid between the upstream capacitor 380 and the intermediate capacitor 384, the downstream resistance 388 of the conductive liquid between the downstream capacitor 382 and the intermediate capacitor 384, external resistance 390 connected to terminal 364 in the upstream branch and external resistance 392, connected to terminal 366 in the downstream branch. The common ends of resistances 390 and 392 and terminal 368 are connected to opposite sides of alternating voltage source 393 through leads 367 and 391. The voltage at point 364 is proportional to the current through resistor 390. It is amplified in amplifier 394 and fed to phase-sensitive detector 396, which extracts the component which is in-phase with the excitation voltage. The voltage at point 366 is proportional to the current through resistor 392. It is amplified in amplifier 398 and fed to phase-sensitive detector 400, which extracts the component which is in-phase with the excitation voltage. The outputs of phase-sensitive detectors 396 and 400 are fed through leads 397 and 399 to differential amplifier 402 which provides an output voltage at terminal 403 that is proportional to the difference between upstream resistance 386 and downstream resistance 388 of the conductive liquid, which is indicative of the presence of a gas bubble in the fluid transfer line 370.

For a 0.375 ini OD polyvinyl chloride tube with a 0.062 in. wall and an electrode length of 1 cm, the capacitances of capacitors 380, 382 and 384 are on the order of 12 picofarads. At a reasonable excitation frequency of 10 MHz, the corresponding capacitive reactance is approximately 1300 ohms. The resistance of a 1 cm long section of conductive liquid along the tube axis between the electrodes is on the order of 220 ohms. A change of resistance of 200 ohms would carry only a change of impedence of 1%. If the liquid were completely replaced by air, that is the tubular space between electrodes were completely filled by an air bubble, the capacitive reactance across the air bubble would be 30 times those of the coupling capacitors and a large signal would be produced.

Phase sensitive detection of the in-phase component of the bridge output voltages can be accomplished by obtaining a voltage in quadrature with the resistive component, rectifying it and integrating the output signal between 90 and 270 degrees of the quadrature signal. Alternatively, the output signal could be sampled at the cross-over point of the quadrature voltage to provide the peak amplitude of the resistive component.

For detection of large air bubbles that fill the transfer line section, similar to detection by existing commercial bubble detectors, the capacitively coupled system can use a simple bridge circuit. For detection of smaller bubbles, phase sensitive detection should be used, as explained above.

As described previously in System C or C-1 operation, flow rate of the liquid infusate is measured by sensing the pressure drop across a (disposable) restrictor in the fluid transfer (IV) line (i.e. transferred fluid). Restrictors with linear characteristics (i.e. pressure drop vs. flow rate) are desirable, as fewer are required to cover a wide range of flow rates, and also because the linearity simplifies the spot calibration by the microcomputer, which eliminates effects of restrictor variations and variations in infusate viscosity. This can be accomplished by passing a known volume of infusate through the restrictor prior to use after it is connected to the differential pressure transducer. The computer senses and integrates the flow rate to attain the calculated volume. The ratio of calculated to measured volume is stored as a calibration coefficient.

To minimize non-linearity for a capillary restrictor, it is necessary that the pressure taps be located on the capillary a sufficient distance from the entrance and exit that laminar flow is fully developed. To achieve this, a restrictor was prepared by casting acrylic around a fine piano wire, which was subsequently removed to provide a uniform capillary bore. Pressure taps were drilled directly into the bore through the acrylic eliminating end effects. A flow sensing restrictor with a 0.016 in. bore made by this technique was tested, and it provided a linear characteristic over a 5:1 range; 100 to 500 cc/hr.

Although commercial devices are available for safe sensing of infusate, as discussed above, these either have functional drawbacks or are too expensive. Considerable experimental work has been performed on means to transmit infusate pressures to remote transducers without affecting sterility, introducing air into the IV line, or damaging transducers.

Tests have been conducted with pressure taps connected directly to the transducer through small bore tubing, pressure being transmitted by liquid compression of air in the tubing. Although there were no instances of air escaping into the IV line, or liquid entering the transducer ports, there is no guarantee that either of these two conditions could not happen.

A pressure-transmitting device has been constructed using a rubber balloon as a barrier. The barrier was found to have a linear liquid pressure vs. air pressure relationship, as long as the balloon remained unstretched. The balloon barrier has since been replaced by a ¾ in. convoluted diaphragm, to minimize size requirements.

Isolating pressure taps shown in FIG. 2 include membranes 42 and 44, which are shown as balloons made of a flexible material. Tests of such a balloon type of pressure transmitter showed a linear liquid pressure vs. air pressure relationship across the balloon with a small transmission loss as long as the balloon remained unstretched. This is accomplished by minimizing the air volumes in the housings around the balloons and the small bore lines connecting the pressure transmitters to the differential transducer.

FIGS. 26 and 27 show a more compact type of flow sensing capillary with integral membrane barrier flow transmitters. A cast acrylic capillary 404 with a fine bore 406 communicates with isolation chambers 408 and 410 through pressure taps 412 and 414, which are located sufficiently far from inlet 416 and outlet 418 to assure the existence of fully developed laminar flow at the pressure taps. Flexible diaphragms 420 and 422, here shown with convolutions, transmit the liquid pressures into air pressures at sensing ports 424 and 426. The pressure loss across the diaphragm is very low due to the convolution and the small residual volumes of the isolation chambers. Any pressure loss can be compensated by a computer correction so that any resulting error is a second order effect. Conductive metal or graphite inserts 428 and 430 in the pressure taps communicate with electrical terminals 432 and 434, so as to allow connection in a circuit as an electrical impedance air bubble detector. The assembly in FIGS. 26 and 27 can be made of a few inexpensive simple molded parts to provide a dual function as a capillary flow sensor and an electrical impedance bubble detector.

Pressurizable containers have been built and pressure cuffs used to permit the non-gravity-dependent infusion system to be used with standard, commercially available products, and not to be dependent on special bags or containers. The application of the non-gravity-dependent infusion system, however, would be simplified by the provision of IV bags, prepackaged in pressurizable enclosures. Some commercial IV bags are supplied with a staff parchment-like translucent cover. This could just as easily be a rigid, pressurizable cover with a protruding outlet port, within a sterile removable seal. The cost of such a cover would be negligible, as evidenced by the plastic bottles and jugs in which water and other drinks are sold in supermarkets.

FIGS. 28 and 29 illustrate how a standard IV bag 436 could be supplied in a pressurizable enclosure 438. The outlet port 440 is similar to that of the present commercial bag. A simple gas pressurization port 442 is provided in the enclosure 438. It should be noted that for any non-gravity-dependent infusion system, where an IV bag is used, some such enclosure is desirable for safe mounting of the IV container, even if the system does not use air pressurization. The inexpensive pressurizable enclosure also provides ease and protection in handling and storage of the IV fluid bags.

Figure 31:
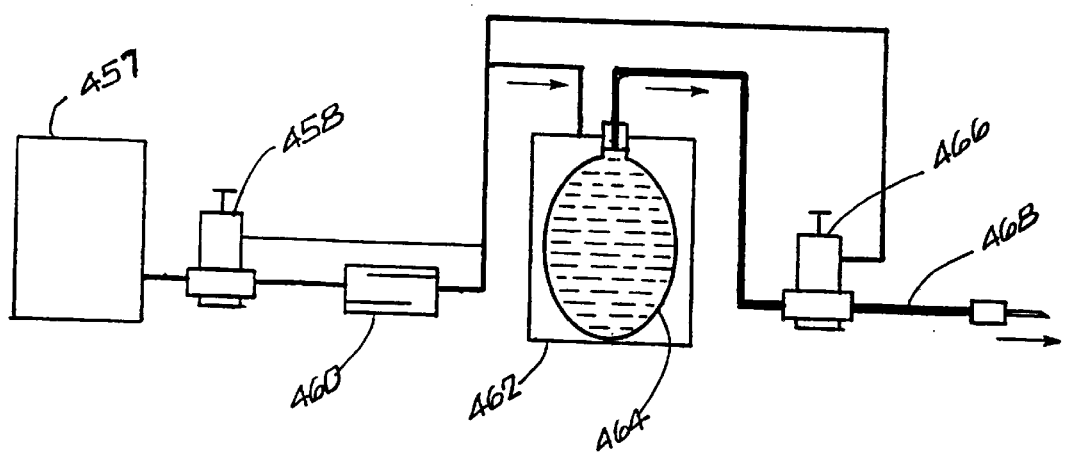
FIG. 31 is a schematic diagram of another pneumatically operated system configured for Type A operation.
Figure 30:
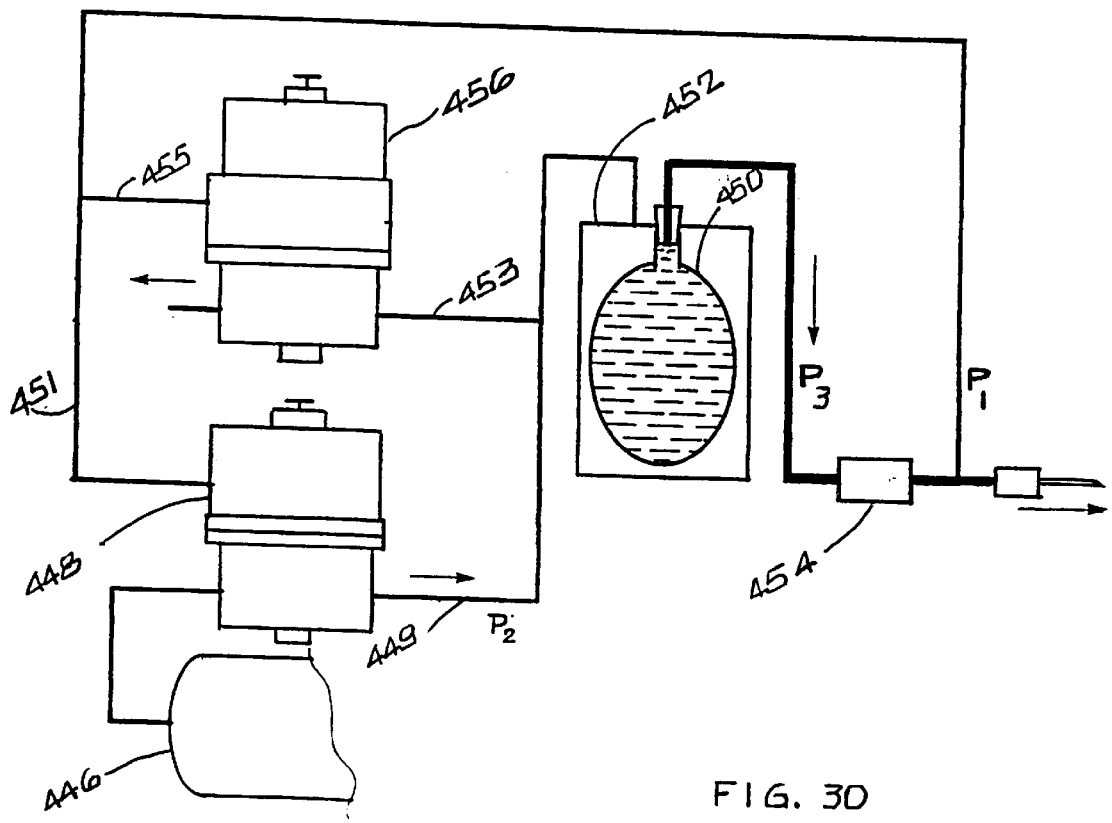
FIG. 30 is a schematic diagram of an entirely pneumatically operated system configured for Type C operation.

FIGS. 30 and 31 show two embodiments of a system for operating a miniature device containing solely pneumatic controls from a small, lightweight compressed air bottle under field conditions for emergency and military use. The system in FIG. 30 is configured for Type C operation and that in FIG. 31 is configured for Type A operation.

In both types of system, the infusion fluid is contained in a flexible bar, which is pressurized to provide the desired flow of infusate in a controlled manner. In System A the intravenous solution (IV) bag is held within a rigid pressurizable enclosure. Air is added to the pressurized chamber at a constant selected mass rate of flow, and the pressure in the chamber is maintained at a constant pressure. As explained previously, under these conditions, infusion liquid must also flow from the IV bag at a constant flow rate. In the pneumatic system, air flow to the chamber is controlled by a regulator which maintains a constant differential air pressure across a restriction in the air line to the pressurized chamber, and the chamber pressure is maintained at a constant pressure by a second regulator operative in the liquid line from the IV bag.

In System C, the IV bag can be pressurized within a rigid enclosure, described for System A, or it can be pressurized by a flexible cuff. The differential pressure across a restriction in the liquid line is controlled by a regulator, which varies air pressure to the bag pressurizing means so as to maintain the differential pressure across the restriction, and, therefore, the liquid flow rate, at constant values.

Referring to FIG. 30, air is supplied from a pressurized tank 446 to a differential pressure regulator 448, here shown as a diaphragm type, which controls the pressure applied through line 449 to an IV bag 450 within a pressurizable container 452.

The differential pressure sensed by regulator 448 is the container pressurizing air pressure, $P_2$, minus the downstream infusion fluid pressure, $P_1$, of a capillary flow sensor 454, which is applied to regulator 448 through line 451. To maintain the fluid flow rate at a constant value, it is desired to maintain the pressure differential, $P_3-P_1$, across the flow sensor at a constant value. It has been shown that the wall stiffness of an IV bag is very low, so that the difference between the air pressure surrounding the bag 450 and the pressure of the fluid within the bag is very small compared to the pressure drop across the capillary flow sensor 454. Thus, $P_2-P_1$, sensed by the regulator diaphragm, is approximately equal to $P_3-P_1$, the drop across the flow sensor, and the regulator effectively controls the differential infusion fluid pressure across the capillary flow sensor.

A major purpose of the differential pressure regulator is to maintain constant flow rate as the bag is depleted of water and the container air pressure begins to drop. When this happens, flow rate drops, $P_2-P_1$, decreases, the regulator spring forces the diaphragm downward, opening the regulator valve, thus increasing $P_2$ and restoring $P_2-P_1$ to its set point, within the droop of the regulator.

The regulator should also be able to reduce the container pressure if the flow rate becomes too high. This could occur, for example, if the line to the needle is temporarily occluded. The flow rate will drop and the regulator will increase container pressure in an effort to restore the differential pressure (i.e. flow rate). When the occlusion is released, the differential pressure will be elevated and the flow rate will rise above its set point. The high differential pressure will cause the diaphragm to move upward, closing the regulator valve. The regulator is now inoperative, and it is necessary to wait until the container pressure has dropped sufficiently due to the decrease in volume of infusion fluid within the bag. Although there is some inherent regulation, a substantial time delay can be experienced, to restore the desired flow rate. In order to reduce this delay, the regulator must have a venting capability, so as to reduce as well as increase the air pressure within the container.

The venting capability, and, therefore, container pressure regulation in both directions, is achieved by the introduction into the system of a back pressure regulator 456, connected in parallel with the forward pressure regulator 448 through lines 453 and 455. Both regulators are adjusted at the same set point, and the same pressure differential is applied in the same direction on the diaphragm of the two regulators. Assuming that the forward pressure regulator is regulating normally, the valve of the forward pressure regulator is partially open, throttling the air flow to the pressurized container. If the fluid flow rate, and the differential pressure increase, the valve of the forward regulator moves upward. If the forward regulator valve seats, and forward flow is shut off, further increase of fluid flow causes the diaphragm of the back pressure regulator to move upward, opening the back pressure valve to vent air from the container as required to maintain the differential pressure across the capillary flow sensor at a substantially constant value.

Referring to FIG. 31, pressurizing air is supplied from a pressurized cylinder 457 to a differential pressure regulator 458 which maintains the air pressure differential across restrictor 460 in the air line 459 to pressurizable container 462 at a constant value. The air pressure in container 462 that pressurizes the infusion fluid in bag 464 is maintained at a constant value by back pressure regulator 466 in flu line 468, thus maintaining the volume change of the liquid fluid as well as the pressurizing gas at a constant value.

What is claimed is:

1. A system for controlled transfer of at least two fluids through lines between at least two reservoirs and a vessel in a manner to provide respective flow-related parameters at selected values, comprising:

（a) a first pressurizable reservoir to contain a quantity of said first fluid;

(b) a fluid vessel to contain a different quantity of said first fluid;

(c) a first conduit means connected at one end to said first reservoir and at the other end to said vessel, to transfer said first fluid between them;

(d) means to control the flow of said first fluid in said first conduit, including means to pressurize said first reservoir in a positive or negative sense with respect to atmospheric pressure, to provide a pressure difference between between said first reservoir and said vessel, that will cause fluid to flow in either direction through said first conduit between said first reservoir and said vessel, depending on the sense of the pressure difference;

(e) first reference means to provide an electrical signal related to a selectable value of a flow related parameter for said first fluid;

(f) first means to provide an electrical signal related to the measured value of said flow-related parameter for said first fluid;

(g) first means to compare the electrical signal outputs of said first reference means and said first flow-related parameter measuring means, and to provide an electrical signal output related to their difference;

(h) means, including a microcomputer, responsive to said electrical signal output of said first comparator means to adjust said first fluid flow control means, in a direction and with a magnitude to provide the selected value of said first flow-related parameter;

(i) a second pressurizable reservoir to contain a quantity of a second fluid;

(j) a second conduit means connected at one end to said second reservoir and at the other end to said vessel to transfer said second fluid between said second reservoir and said vessel;

(k) means to control said second fluid in said second conduit means, including means to pressurize said second reservoir;

(l) second reference means to provide an electrical signal related to a selectable value of a flow-related parameter for said second fluid;

(m) second measuring means to provide an electrical signal related to the measured value of said flow-related parameter for said second flank;

(n) second comparator means to compare the electrical signal outputs of said second reference means and said second measuring means, and to provide an electrical signal output related to their difference; and (o) means including a microcomputer, responsive to said electrical signal output of said second comparator means to adjust said second fluid control means in a direction and with a magnitude to provide the selected value of said second flow-related parameter.

2. A controlled fluid transfer system as claimed in claim 1, in which one of said fluid reservoirs is a container with at least one flexible wall, and said reservoir pressurizing means is a pressure applicator with a pneumatically-actuated movable wall in contact with a flexible wall of said container, said pressure applicator being connected to a source of variable pressure that applies to the fluid in said container through said movable wall of said pressure applicator and said flexible wall of said container.

3. A controlled fluid transfer system as claimed in claim 1, in which said pressurizing means for at least one of said reservoirs include a sealed, relatively rigid housing, a source of variable pneumatic pressure, a pneumatic pressurizing port in the wall of said housing pressurizing port, to transfer pressurizing gas between said pneumatic pressure source and the interior of said housing, and in which said reservoir is a container with at least one movable wall, located in the interior of said housing and connected to said fluid transfer conduit means, through a seal in the wall of said housing, so as to cause flow of fluid through said fluid transfer conduit means from said reservoir to said vessel, when said variable pneumatic pressure is positive, and to cause flow of fluid through said fluid transfer conduit means from said vessel to said reservoir when said variable pneumatic pressure is negative.

4. A controlled fluid transfer system as claimed in claim 1, in which one of said flow-related parameters is the fluid flow rate in the corresponding conduit means and said flow-related parameter measuring means include means, having an output, to measure the rate of said fluid through said conduit means.

5. A controlled fluid transfer system as claimed in claim 1, in which one of said flow related parameters is the change of fluid volume in one of said reservoirs.

6. A controlled fluid transfer system as claimed in claim 4, in which said fluid flow rate measuring means include a measuring restrictor in said fluid flow conduit means and a transducer with an electrical output related to the fluid pressure drop across said restrictor as a measure of the flow rate of said fluid.

7. A controlled fluid transfer system as claimed in claim 1, in which one of said flow control means include adjustable valve means in the corresponding conduit means to vary the resistance to flow of said fluid between said reservoir and said vessel.

8. A controlled fluid transfer system as claimed in claim 1, in which one of said reservoir pressurizing means are adjusted to provide the selected value of the corresponding flow-related parameter.

9. A controlled fluid transfer system as claimed in claim 1, in which said valve means are adjusted to provide the selected value of said flow-related parameter.

10. A controlled fluid transfer system as claimed in claim 9, in which one of said reservoir pressurizing means are adjusted to maintain the pressure of said reservoir at a constant selected value.

11. A controlled fluid transfer system as claimed in claim 3, in which one of said fluid control means include control means include adjustable valve means in the corresponding means to vary the resistance to flow of said fluid between said reservoir and said vessel, said valve means are adjusted to maintain the pneumatic pressure in the interior of said housing at a constant selected value, and said source of variable pneumatic pressure is adjusted to maintain the pneumatic mass rate of flow in said gas transfer line between said source and the interior of said housing and through said port at a constant value required to maintain the flow rate of fluid in said conduit means between said reservoir and said vessel at the selected value.

12. A controlled fluid transfer system as claimed in claim 3, in which at least one of said fluid control means include a restriction in said fluid transfer conduit means between said reservoir and said vessel, means to activate said source of variable pneumatic pressure when said pneumatic pressure in the interior of said housing reaches a lower limit value of a positive or a negative sense, to provide gas flow through said gas transfer line between said pneumatic pressure source and the interior of said housing, and to de-activate said pneumatic pressure source when said pneumatic pressure reaches an upper limit value, and means to sense the time for the pneumatic pressure to decay from said upper pressure limit to said lower pressure limit as a measure of the rate of flow of said fluid in said fluid in said fluid transfer conduit means between said reservoir and said vessel.

13. A controlled fluid transfer system as claimed in claim 3, in which at least one of said flow-related parameter means include means to measure the volumetric flow rate of said fluid in the corresponding fluid transfer conduit means; said fluid flow rate measuring means, having an output, to measure the volumetric flow rate of the gas in said gas transfer line, at a location in said line where the rate of the gas in said gas transfer line, at a location in said line where the difference between the gas pressure at said flow rate measuring location and the gas pressure in the interior of said housing is small compared to their absolute value; means, having an output, responsive to the outputs of said gas flow rate measuring means and said gas pressure measuring means to compute the volumetric flow rate of said fluid in said fluid transfer conduit means in accordance with the following equations:

$$V_h = V_o + \int_o^t Q_f \, dt$$

where $Q_f$ is the computed volumetric flow rate of said fluid in said fluid transfer line, $Q_L$ is the measured volumetric flow rate of the gas in said gas transfer line at said flow rate measuring locations, $V_h$ is the volume occupied by the gas in said housing, exterior to said reservoir, $P_g$ is the measured gas pressure, $V_o$ is the residual volume occupied by the gas in said housing when said reservoir is full.

14. A controlled fluid transfer system as claimed in claim 13, including means, having an output, to compute the volume of said fluid transferred through the fluid transfer conduit means as the time integral of the computed field volumetric flow rate.

15. A controlled fluid transfer system as claimed in claim 13, in which said gas flow rate measuring means is a gas flow sensor in said gas transfer line, whose output is an electrical signal, said gas pressure measuring means is a gas pressure transducer whose output is an electrical signal, and said fluid flow rate computing means is a microcomputer, whose inputs are the electrical signal from said gas flow sensor, the electrical signal from said gas pressure transducer, and an initial electrical input proportional to the value of the residual gas volume in said housing.

16. A controlled fluid transfer system as claimed in claim 1, in which said fluid is liquid, including non-gravity-dependent means in each of said fluid transfer conduit means to effectively separate gas bubbles from said liquid flowing through said gas separating means in any orientation.

17. A controlled fluid transfer system as claimed in claim 1, in which said fluid is a liquid, including means in each of said fluid transfer conduit means to detect the passage of gas bubbles in said liquid flowing through said fluid transfer conduit means.

* * * * *